US010690684B2

(12) United States Patent
Macintyre et al.

(10) Patent No.: US 10,690,684 B2
(45) Date of Patent: *Jun. 23, 2020

(54) APPARATUS AND SYSTEM FOR MEASURING VOLUME OF BLOOD LOSS

(71) Applicant: University of Utah Research Foundation, Salt Lake City, UT (US)

(72) Inventors: Annette Macintyre, Salt Lake City, UT (US); Lara Brewer Cates, Bountiful, UT (US); Suzanne Wendelken, Salt Lake City, UT (US); Quinn Tate, North Salt Lake, UT (US); Soeren Hoehne, Salt Lake City, UT (US); Alfred Akerman, Knoxville, TN (US); Stephen W. Allison, Collierville, TN (US); Matthew B. Scudiere, Oak Ridge, TN (US); Michael R. Cates, Oak Ridge, TN (US); David L. Beshears, Knoxville, TN (US); Adan James Akerman, Knoxville, TN (US)

(73) Assignees: Majelco Medical, Inc., Woods Cross, UT (US); University of Utah Research Foundation, Salt Lake City, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/157,719

(22) Filed: Oct. 11, 2018

(65) Prior Publication Data

US 2019/0041405 A1 Feb. 7, 2019

Related U.S. Application Data

(63) Continuation-in-part of application No. 16/055,745, filed on Aug. 6, 2018, which is a continuation of
(Continued)

(51) Int. Cl.
*G01N 33/72* (2006.01)
*G01N 33/49* (2006.01)
(Continued)

(52) U.S. Cl.
CPC ....... *G01N 33/721* (2013.01); *A61B 5/02042* (2013.01); *A61B 5/1455* (2013.01);
(Continued)

(58) Field of Classification Search
None
See application file for complete search history.

(56) References Cited

U.S. PATENT DOCUMENTS

| 2,386,878 A | 1/1944 | Nickerson |
| 3,068,742 A | 12/1962 | Hicks, Jr. et al. |

(Continued)

FOREIGN PATENT DOCUMENTS

| WO | WO2001017421 | 3/2001 |
| WO | WO2013173356 | 11/2013 |

(Continued)

OTHER PUBLICATIONS

Zijlstra WG, Van Kampen E. Standardization of hemoglobinometry. I. The extinction coefficient of hemiglobincyanide. Clin. Chim. Acta. Sep. 1960; 5:719-26.
(Continued)

*Primary Examiner* — Shawn Decenzo
(74) *Attorney, Agent, or Firm* — Morriss O'Bryant Compagni Cannon, PLLC

(57) ABSTRACT

A system for measuring the blood loss comprises a measuring device that determines the hemoglobin concentration of fluid within a container utilizing a light source and a light detector. The container receives blood and other fluids from a patient during a medical procedure. Light from the light source is passed through the blood and other fluids in the
(Continued)

container and is detected by the light detector. Based upon a magnitude of light detected, the hemoglobin concentration of the fluid in the container can be determined. A volume-measuring device determines the volume of blood and fluid in the container. Knowing the hemoglobin concentration and volume of fluid in the container, the volume of patient blood loss in the container can be determined. The blood loss measuring device in combination with infusion systems maintains a real-blood volume status so that proper infusion of blood, crystalloid and/or colloid solutions occurs.

20 Claims, 11 Drawing Sheets

Related U.S. Application Data application No. 14/890,098, filed as application No. PCT/US2014/037448 on May 9, 2014, now Pat. No. 10,041,960, application No. 16/157,719, which is a continuation of application No. 15/485,070, filed on Apr. 11, 2017, now Pat. No. 10,285,596.

(60) Provisional application No. 61/821,937, filed on May 10, 2013, provisional application No. 62/320,991, filed on Apr. 11, 2016.

(51) Int. Cl.
  *G01N 21/31* (2006.01)
  *A61M 1/00* (2006.01)
  *A61B 5/1455* (2006.01)
  *A61B 5/145* (2006.01)
  *A61B 5/02* (2006.01)
  *G01N 21/85* (2006.01)

(52) U.S. Cl.
  CPC ....... *A61B 5/14546* (2013.01); *A61M 1/0001* (2013.01); *A61M 1/006* (2014.02); *G01N 21/31* (2013.01); *G01N 21/314* (2013.01); *G01N 21/8507* (2013.01); *G01N 33/49* (2013.01); *A61M 2205/331* (2013.01); *A61M 2205/3313* (2013.01); *A61M 2205/3331* (2013.01); *A61M 2205/3389* (2013.01); *G01N 2021/8535* (2013.01); *G01N 2333/805* (2013.01)

(56) References Cited

U.S. PATENT DOCUMENTS

| | | | |
|---|---|---|---|
| 3,296,922 A | | 1/1967 | Goldberg |
| 3,814,081 A | * | 6/1974 | Mori .................. A61B 5/02154 356/41 |
| 3,995,168 A | | 11/1976 | Neuscheler et al. |
| 4,305,659 A | | 12/1981 | Bilstad et al. |
| 4,562,842 A | | 1/1986 | Morfeld et al. |
| 4,773,423 A | | 9/1988 | Hakky |
| 4,810,090 A | | 3/1989 | Boucher et al. |
| 4,904,878 A | | 2/1990 | Gipp et al. |
| 4,954,724 A | | 9/1990 | Koda et al. |
| 5,029,584 A | | 7/1991 | Smith |
| 5,048,524 A | | 9/1991 | Bailey |
| 5,231,032 A | | 7/1993 | Ludvigsen |
| 5,236,664 A | | 8/1993 | Ludvigsen |
| 5,709,670 A | * | 1/1998 | Vancaillie .......... A61B 5/02042 600/573 |
| 5,734,464 A | | 3/1998 | Gibbs |
| 5,773,301 A | | 6/1998 | Ziegler |
| 5,944,668 A | | 8/1999 | Vancaillie et al. |
| 6,064,474 A | | 5/2000 | Lee et al. |
| 6,291,824 B1 | | 9/2001 | Battarbee et al. |
| 6,718,190 B2 | | 4/2004 | Krivitski et al. |
| 6,831,733 B2 | | 12/2004 | Pettersson et al. |
| 7,119,689 B2 | | 10/2006 | Mallett et al. |
| 7,710,567 B1 | | 5/2010 | Mentzer et al. |
| 7,981,073 B2 | | 7/2011 | Mollstam et al. |
| 8,072,594 B1 | | 12/2011 | McMahon |
| 8,219,170 B2 | | 7/2012 | Hausmann et al. |
| 8,493,441 B2 | | 7/2013 | Thonhauser |
| 2002/0058342 A1 | | 5/2002 | Lilja et al. |
| 2003/0123047 A1 | | 7/2003 | Pettersson et al. |
| 2005/0065820 A1 | | 3/2005 | Mallett et al. |
| 2005/0209585 A1 | | 9/2005 | Nord et al. |
| 2005/0243303 A1 | | 11/2005 | Pettersson et al. |
| 2006/0013725 A1 | | 1/2006 | Larsen |
| 2006/0177347 A1 | | 8/2006 | Larsen et al. |
| 2006/0280216 A1 | | 12/2006 | Jayaraman |
| 2007/0060809 A1 | * | 3/2007 | Higgins ............... A61B 5/0075 600/328 |
| 2007/0135779 A1 | | 6/2007 | Lalomia et al. |
| 2008/0071154 A1 | | 3/2008 | Hausmann et al. |
| 2008/0179344 A1 | | 7/2008 | Michaels et al. |
| 2009/0054908 A1 | | 2/2009 | Zand et al. |
| 2009/0075324 A1 | | 3/2009 | Pettersson |
| 2009/0115996 A1 | * | 5/2009 | Serebrennikova ....... C12Q 1/04 356/39 |
| 2009/0187131 A1 | | 7/2009 | Fitzgerald et al. |
| 2009/0240119 A1 | | 9/2009 | Schwaibold et al. |
| 2010/0134303 A1 | | 6/2010 | Perkins |
| 2010/0160754 A1 | | 6/2010 | Durkin et al. |
| 2010/0249550 A1 | | 9/2010 | Lovejoy |
| 2010/0298658 A1 | | 11/2010 | McCombie et al. |
| 2011/0063433 A1 | | 3/2011 | Thonhauser |
| 2011/0112435 A1 | | 5/2011 | Ramanujam et al. |
| 2012/0035417 A1 | | 2/2012 | Mollstam et al. |
| 2012/0097567 A1 | * | 4/2012 | Zhao ..................... A47G 23/16 206/459.1 |
| 2012/0113411 A1 | * | 5/2012 | Li ...................... A61B 5/14552 356/41 |
| 2013/0006116 A1 | | 1/2013 | Kim et al. |
| 2013/0301901 A1 | | 11/2013 | Satish et al. |
| 2013/0303870 A1 | | 11/2013 | Satish et al. |
| 2013/0338458 A1 | | 12/2013 | Bechtel et al. |
| 2014/0128838 A1 | | 5/2014 | Satish et al. |
| 2015/0168371 A1 | * | 6/2015 | Babson ................. G01N 21/31 356/40 |
| 2016/0022209 A1 | * | 1/2016 | Fraisl ....................... A45F 3/16 600/590 |
| 2016/0123998 A1 | * | 5/2016 | MacIntyre ........ A61B 5/02042 436/66 |
| 2016/0331282 A1 | * | 11/2016 | Satish .............. A61B 5/150099 |
| 2018/0106656 A1 | * | 4/2018 | Simon .................... G01F 22/02 |

FOREIGN PATENT DOCUMENTS

| | | | |
|---|---|---|---|
| WO | WO2014183003 | 11/2014 | |
| WO | WO-2014183003 A1 * | 11/2014 | ......... A61B 5/02042 |
| WO | WO2015173611 | 11/2015 | |

OTHER PUBLICATIONS

Vanzetti G. An azide-methemoglobin method for hemoglobin determination in blood. J Lab Clin Med. Jan. 1966; 67(1):116-26.
Oshiro I, Takenaka T, Maeda J. New method for hemoglobin determination by using sodium lauryl sulfate (SLS). Clin Biochem. Apr. 1982; 15(2):83-8.
Lewis SM, Garvey B, Manning R, Sharp SA, Wardle J. Lauryl sulphate haemoglobin: a non-hazardous substitute for HiCN in haemoglobinometry. Clin Lab Haematol. 1991; 13(3):279-90.
Mainland, J.F., British Journal of Anaesthesia 1966, 38, 76-78.
Brant, H. A. et al, Journal of Obstetrics and Gynaecology of the British Commonwealth 1966, 73, 456-459.
Paton, J.S. et al., Lancet 1977, 310, 744-745.
Lewis, S.M. et al., Lauryl sulphate haemoglobin; a non-hazardous substitute for HiCN in haemoglobinometry. Clin Lab Haematol. 1991; 13(3):279-90.
Oshiro, L. et al., New method for hemoglobin determination by using sodium lauryl sulfate (SLS). Clin Biochem. 1982; 15(2):82-8.

(56) References Cited

OTHER PUBLICATIONS

Vanzetti, G., An azide-methemoglobin method for hemoglobin determination in blod. J Lab Clin Med. 1966; 67(1):116-26.
Zijlstra, W.G. et al., Standardization of hemoglobinometry. I. The extinction coefficient of hemiglobincyanide. Clin Chim Act. 1960; 5:719-26.
International Search Report and Written Opinion dated Sep. 26, 2014 for Application No. PCT/US2014/037448, which was filed on May 9, 2014 and published as WO 2014/183003 on Nov. 13, 2014 (Applicant—University of Utah Research Foundation.) (11 pages).
International Preliminary Report on Patentability dated Nov. 10, 2015 for Application No. PCT/US2014/037448, which was filed on May 9, 2014 and published as WO 2014/183003 on Nov. 13, 2014 (Applicant—University of Utah Research Foundation. (9 pages).
European Search report and Written Opinion dated Dec. 1, 2016 by the International Searching Authority for EP Application No. 14794433.4 on May 9, 2014 and published as 2994042 on Mar. 16, 2016 (Applicant—University of Utah Research Foundation; (6 pages).
von Schenck, H. et al., Clinical Chemistry 1986, 32, 526-529.

\* cited by examiner

APPARATUS AND SYSTEM FOR MEASURING VOLUME OF BLOOD LOSS

CROSS-REFERENCE TO RELATED APPLICATIONS

The present application is a continuation-in-part of U.S. patent application Ser. No. 16/055,745, filed Aug. 6, 2018, which is a continuation of U.S. patent application Ser. No. 14/890,098, filed Nov. 9, 2015, now U.S. Pat. No. 10,041,960, which is a national phase entry under 35 U.S.C. § 371 of International Application No. PCT/US2014/037448, filed May 9, 2014, which claims the benefit of the filing date of U.S. Provisional Patent Application No. 61/821,937, filed May 10, 2013, and a continuation of U.S. patent application Ser. No. 15/485,070, filed Apr. 11, 2017, which claims priority to U.S. Provisional Patent Application No. 62/320,991, filed on Apr. 11, 2016, the entirety of each of which is hereby incorporated by reference.

BACKGROUND OF THE INVENTION

Field of the Invention

This invention relates to devices, systems, and methods for measuring blood loss of a subject, and more particularly, to devices, systems, and methods for measuring the blood loss of a subject during a surgical procedure.

State of the Art

During surgical procedures, it is often necessary to assess the amount of patient blood loss in order to determine whether a transfusion of blood or other intravenous fluid is needed to maintain proper blood/fluid levels of the patient. Unnecessary blood transfusions, coupled with over/under administration of IV fluids, however, are frequently associated with poor patient outcomes. During such medical procedures, blood, irrigation fluids and other bodily fluids are collected in a suction canister. As such fluids collect in the suction canister, conventional methods of estimating blood loss requires operating personnel to estimate the amount of blood contained in the suction canister by visual inspection. Because the suction canister most often includes unknown quantities of other fluids in addition to blood, such visual estimates can be quite inaccurate.

While the majority of the blood lost by the patient in surgery is collected in the suction canister, the primary method for assessing the volume of blood in a suction canister during surgery is to use a combination of visual assessment of the volume reading on the canister and knowledge of how much irrigation fluid has been used during fluid suctioning. The volume of irrigation fluid is then subtracted from the volume in the canister to determine how much fluid in the canister is blood and is based on an inaccurate assumption that any fluid that is not irrigation fluid must be blood. Visual assessment of blood in the suction canister is also not accurate and requires a visual assessment by a member of the surgical team, yet remains the primary method of assessment today.

Other attempts in the art to determine the amount of blood in the suction canister have included the use of a digital scale to weigh the suction canister and surgical sponges in order to estimate blood loss. More recently, a photographic method has been employed based on digital photography in which a digital image taken by a smartphone or similar handheld device is used to measure hemoglobin in surgical sponges. Attempts have also been made to use this method with a suction canister as well.

During many surgical procedures blood loss can be significant and must be carefully monitored to ensure that the patient maintains proper and sufficient fluid levels during such procedures. Blood, bodily tissue, bone fragments and other fluids and materials are removed from the surgical cite by suction. In addition, saline solution is used to irrigate the surgical site during an operation and thus will accompany the removal of blood, bodily tissue, bone fragments and other fluids and materials removed by suction. These materials and fluids are collected in the suction canister during the operation. When the volume of blood loss reaches a threshold level, a transfusion is typically required. Excessive blood loss without such transfusions can lead to serious complications or death. It is therefore important to monitor the blood-saline (and other possible constituents) mixture to determine a more precise volume of blood that has been lost by the patient during a medical procedure. If the volume of blood lost can be continuously and quickly monitored, blood loss rates can also be determined.

A typical canister tree in an operating room can hold six to eight suction canisters. A surgery with medium-level blood loss will require one to three 2 L suction canisters. As one canister becomes full, fluids being removed by suction are switched to the next available canister. The suction canisters are made to be disposable and currently cost approximately $1.30 each. Thus, it would be desirable for any blood-measuring device that may be part of or included with the canister to also be relatively inexpensive and disposable so that the entire unit can be discarded when the medical procedure is finished. Since operating rooms and surgical procedures can be tedious, active, crowded by the presence of the attending surgical team, and require rapid decision making, it is also desirable to have a blood monitoring system that is easy to use and provides real time and easily observable blood loss readouts.

Thus, there is a need in the art for a device, system and method for accurately and quickly measuring the blood loss of a subject during a surgical procedure. The present invention satisfies this need by combining a fiber-optic based light emitter or other similar light source and sensor to determine hemoglobin concentration in a fluid mixture within a suction canister along with either a micro-electromechanical (MEMS) sensor to measure fluid pressure within the suction canister or an optical method contained within the sensor that measures fluid levels from which the volume of the fluid mixture within the suction canister can be determined. By knowing the hemoglobin concentration and total fluid volume within the suction canister, the volume of blood loss of a patient can be accurately determined in real time.

SUMMARY OF THE INVENTION

The present invention comprises a blood measurement device for determining the amount of blood of a subject within a fluid sample. The blood measurement device includes a light source, at least one light sensor, such as a photodetector, and a processor which analyzes the signals arising from the light source and the at least one light sensor. The light source is configured to selectively generate light at two or more different wavelength bands. The light source and the at least one light sensor are configured for positioning in an operative position. In the operative position, the at least one light sensor is configured to receive at least a portion of the light generated by the light source. Upon positioning of the light source and the at least one sensor in the operative position, the at least one light sensor is configured to produce a signal indicative of the absorbance of the fluid sample at a selected number of wavelength bands. Absorbance is a combination of absorption, transmission, scattering, and fluorescence. The processor is operatively coupled to the at least one light sensor and is configured to receive the signals from the at least one light sensor. Based upon the signal from a selected number wavelength bands, the processor can be configured to determine the concentration of hemoglobin within the fluid sample. Optionally, the processor can be further configured to determine the volume of blood within the fluid sample The blood measurement system may also include a volume sensor to provide total fluid volume within the container, such as a suction canister, in which the hemoglobin concentration is being determined according to the present invention. By knowing the hemoglobin concentration and the volume of fluid in the container, the volume of patient blood within the container can be determined.

Also disclosed are blood measurement systems including the blood measurement device and a container, such as a suction canister. Optionally, portions of the blood measurement device can be selectively insertable within a fluid sample positioned within the suction canister.

Methods of determining the blood loss of a subject are also disclosed. The methods can include operatively positioning the blood measurement device relative to a fluid sample and using the blood measurement device (alone or in combination with conventional methods) to determine the concentration of hemoglobin within the fluid sample. Optionally, the methods can include administering one or more reagents to the interior space of the suction canister. Optionally, the reagents can be configured to convert hemoglobin within the fluid sample into either methemoglobin or sulphemoglobin. The methods can optionally include the step of delivering an anti-coagulant to the fluid sample.

These and other advantages and features of the invention are more fully described in the detailed description of the invention with reference to the drawings. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE DRAWINGS

When considered in connection with the following illustrative figures, a more complete understanding of the present invention may be derived by referring to the detailed description. In the figures, like reference numbers refer to like elements or acts throughout the figures.

DETAILED DESCRIPTION OF THE INVENTION

Figure 1:
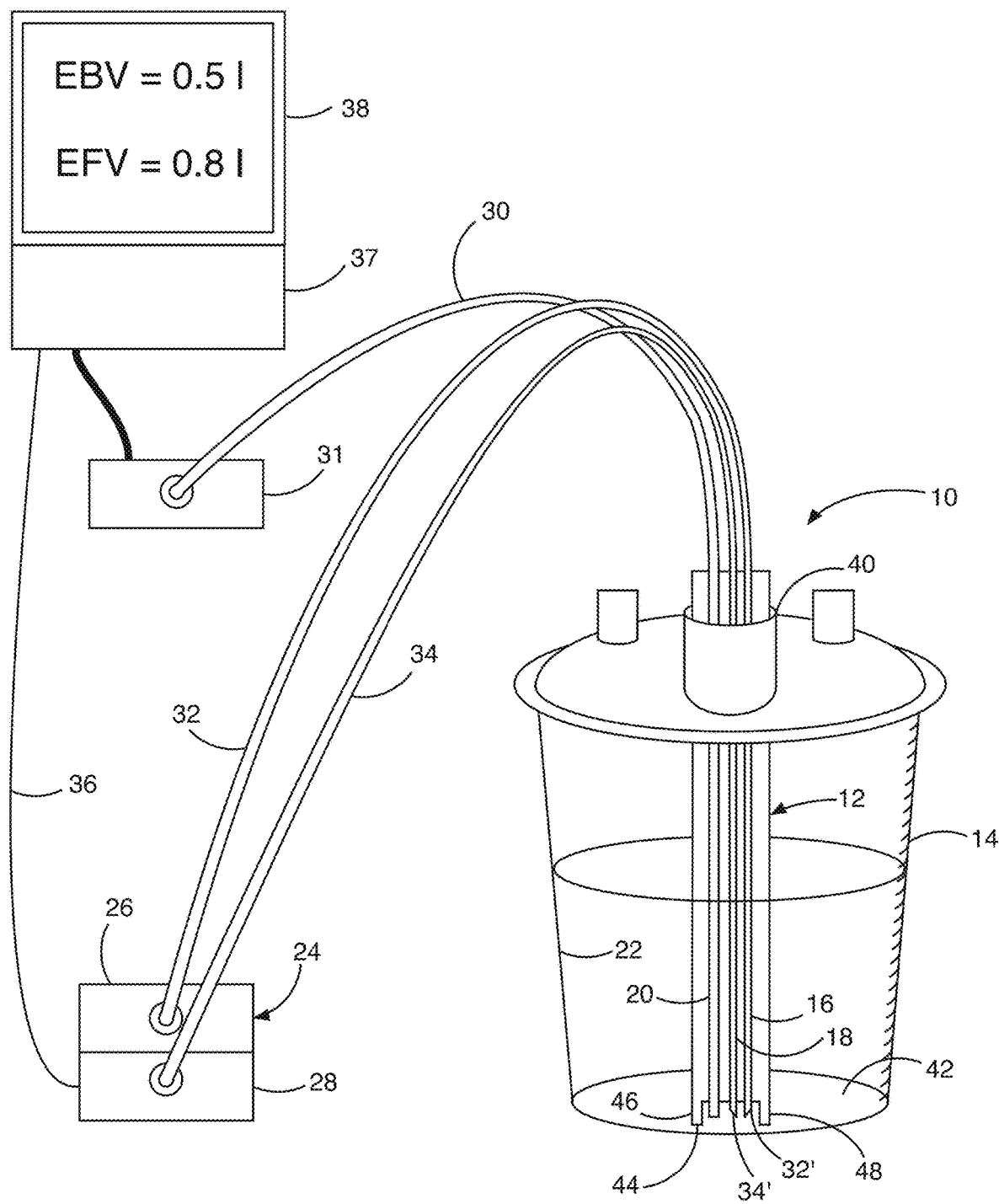
FIG. 1 is a front side view of a blood volume measuring apparatus in accordance with the principles of the present invention.

The present invention can be understood more readily by reference to the following detailed description, examples, drawings, and claims, and their previous and following description. However, before the present devices, systems, and/or methods are disclosed and described, it is to be understood that this invention is not limited to the specific devices, systems, and/or methods disclosed unless otherwise specified, as such can, of course, vary. It is also to be understood that the terminology used herein is for the purpose of describing particular aspects only and is not intended to be limiting.

The following description of the invention is provided as an enabling teaching of the invention in its best, currently known embodiment. To this end, those skilled in the relevant art will recognize and appreciate that many changes can be made to the various aspects of the invention described herein, while still obtaining the beneficial results of the present invention. It will also be apparent that some of the desired benefits of the present invention can be obtained by selecting some of the features of the present invention without utilizing other features. Accordingly, those who work in the art will recognize that many modifications and adaptations to the present invention are possible and can even be desirable in certain circumstances and are a part of the present invention. Thus, the following description is provided as illustrative of the principles of the present invention and not in limitation thereof.

Unless specifically noted, it is intended that the words and phrases in the specification and the claims be given their plain, ordinary, and accustomed meaning to those of ordinary skill in the applicable arts. It is noted that the inventor can be his own lexicographer. The inventors expressly elect, as their own lexicographers, to use only the plain and ordinary meaning of terms in the specification and claims unless they clearly state otherwise and then further, expressly set forth the "special" definition of that term and explain how it differs from the plain and ordinary meaning. Absent such clear statements of intent to apply a "special" definition, it is the inventor's intent and desire that the simple, plain and ordinary meaning to the terms be applied to the interpretation of the specification and claims.

The inventors are also aware of the normal precepts of English grammar. Thus, if a noun, term, or phrase is intended to be further characterized, specified, or narrowed in some way, then such noun, term, or phrase will expressly include additional adjectives, descriptive terms, or other modifiers in accordance with the normal precepts of English grammar. Absent the use of such adjectives, descriptive terms, or modifiers, it is the intent that such nouns, terms, or phrases be given their plain, and ordinary English meaning to those skilled in the applicable arts as set forth above.

Further, the inventors are fully informed of the standards and application of the special provisions of 35 U.S.C. § 112, ¶ 6. Thus, the use of the words "function," "means" or "step" in the Detailed Description of the Invention or claims is not intended to somehow indicate a desire to invoke the special provisions of 35 U.S.C. § 112, ¶ 6, to define the invention. To the contrary, if the provisions of 35 U.S.C. § 112, ¶ 6 are sought to be invoked to define the inventions, the claims will specifically and expressly state the exact phrases "means for" or "step for" and the specific function, without also reciting in such phrases any structure, material or act in support of the function. Thus, even when the claims recite a "means for . . . " or "step for . . . " if the claims also recite any structure, material or acts in support of that means or step, or that perform the recited function, then it is the clear intention of the inventor not to invoke the provisions of 35 U.S.C. § 112, ¶ 6. Moreover, even if the provisions of 35 U.S.C. § 112, ¶ 6 are invoked to define the claimed inventions, it is intended that the inventions not be limited only to the specific structure, material or acts that are described in the illustrated embodiments, but in addition, include any and all structures, materials or acts that perform the claimed function as described in alternative embodiments or forms of the invention, or that are well known present or later-developed, equivalent structures, material or acts for performing the claimed function.

In the following description, and for the purposes of explanation, numerous specific details are set forth in order to provide a thorough understanding of the various aspects of the invention. It will be understood, however, by those skilled in the relevant arts, that the present invention may be practiced without these specific details. In other instances, known structures and devices are shown or discussed more generally in order to avoid obscuring the invention. In many cases, a description of the operation is sufficient to enable one to implement the various forms of the invention, particularly when the operation is to be implemented in software. It should be noted that there are many different and alternative configurations, devices and technologies to which the disclosed inventions may be applied. Thus, the full scope of the inventions is not limited to the examples that are described below.

Various aspects of the present invention may be described in terms of functional block components and various processing steps. Such functional blocks may be realized by any number of hardware or software components configured to perform the specified functions and achieve the various results.

As used throughout, the singular forms "a," "an" and "the" include plural referents unless the context clearly dictates otherwise. Thus, for example, reference to "a photodetector" can include two or more such photodetectors unless the context indicates otherwise.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

As used herein, the terms "optional" or "optionally" mean that the subsequently described event or circumstance may or may not occur, and that the description includes instances where said event or circumstance occurs and instances where it does not.

The word "or" as used herein means any one member of a particular list and also includes any combination of members of that list.

As used herein, a "subject" is an individual and includes, but is not limited to, a mammal (e.g., a human, horse, pig, rabbit, dog, sheep, goat, non-human primate, cow, cat, guinea pig, or rodent), a fish, a bird, a reptile or an amphibian. The term does not denote a particular age or sex. Thus, adult and newborn subjects, as well as fetuses, whether male or female, are intended to be included. A "patient" is a subject afflicted with a disease or disorder. The term "patient" includes human and veterinary subjects. As used herein, the term "subject" can be used interchangeably with the term "patient."

Described herein with reference to the figures are devices, systems, and methods for measuring blood loss of a subject. It is contemplated that the disclosed devices, systems, and methods can provide a more accurate measurement of blood loss during a surgical procedure than conventional devices, systems, and methods. As further disclosed herein, the disclosed systems and methods can be used to iteratively estimate the hemodilution of a subject based on the kinetics of intravenous fluid administration and blood loss. It is further contemplated that the disclosed blood measurement devices and systems can directly measure the amount of blood in a suction canister or other fluid collection container based upon the estimated hemodilution of the subject. Thus, it is contemplated that the disclosed system can iteratively estimate the hemoglobin status of the subject intraoperatively by taking into account a baseline estimation of the patient's intravascular blood volume (EBV) and preoperative hemoglobin status, the volume of intravenous fluids administered to the subject, as well as the volume and hemoglobin concentration of the fluid within the suction canister. The updated estimated hemoglobin status of the subject can then be used to accurately calculate the new volume of blood loss in the suction canister.

As further described herein, it is contemplated that the disclosed devices, systems, and methods can optionally employ algorithms to determine the concentration of hemoglobin within a fluid sample and/or the blood loss experienced by a subject during a medical procedure. However, it is contemplated that the disclosed devices, systems and methods can be used in conjunction with any conventional method of predicting a subject's hemoglobin concentration and/or the volume of a fluid sample containing the blood of a subject. Thus, although exemplary algorithms for determining hemoglobin concentration and blood loss are provided herein, it is understood that the devices, systems, and methods disclosed herein are not restricted to use with particular algorithms. For example, when the hemoglobin concentration within a fluid sample and the volume of the fluid sample are known (i.e., provided as an input to the processor of the device or determined by the device), it is contemplated that the disclosed devices, systems, and methods can be used in conjunction with conventional methods for determining one or more of the following: the subject's preoperative hemoglobin concentration; an updated hemoglobin concentration of the subject, determined from a subject's blood sample; an updated hemoglobin concentration of the subject, based upon an estimate provided by a practitioner (e.g., an anesthesiologist); or an updated hemoglobin concentration of the subject, based upon a continuous, non-invasive method as is known in the art. It is contemplated that, when an updated hemoglobin concentration of the subject is determined, the preoperative hemoglobin concentration of the subject can be averaged with the updated hemoglobin concentration to permit determination of the amount of blood lost by the subject. It is further contemplated that the averaged hemoglobin concentration can be provided to a processor as disclosed herein in the form of one or more user inputs.

FIG. 1. Illustrates a first embodiment of a device, system and method to reliably and accurately determine an amount of blood loss by a patient during surgery or other medical procedure. The blood loss measuring system, generally indicated at 10, comprises a single sensor probe assembly 12 that is configured to be inserted, insertable or built into a suction container 14 or other container into which blood from a patient and other fluids are collected during a medical procedure, such as surgery. The probe sensor 12 includes light sensor probes 16 and 18 for determining hemoglobin concentration in mixture with other fluids, such as saline, within the suction container 14 and a pressure sensor probe 20, both of which are in fluid communication with an interior 22 of the suction container 14. The sensor probe assembly 12 is optionally configured to be disposable along with disposable type suction containers. The sensor probe 12 according to the present invention is configured to come into contact with blood and other fluids in the suction container 14 and is configured to be an expendable, low-cost device so that the sensor probe 12 may be discarded after a single use or single medical procedure.

The system 10 also includes a pressure-measuring device, which includes the pressure sensor probe 20 is configured to provide total fluid volume within the container 14. Thus, both the pressure sensor probe and light sensor probes for measuring hemoglobin concentration within the container 14 are incorporated into the single probe 12 that is easily insertable or built into a suction canister or container 14. It should be noted that the terms "container" and "canister" are used interchangeably throughout and are intended to mean the vessel within which blood and other fluids are collected during a medical procedure. The hemoglobin concentration sensor system 24 utilizes the principle of optical absorption to determine a percentage of hemoglobin in the fluid contained within the container 14. Each wavelength of light from a white light source 26 passes through blood and other fluids within the container 14 and is measured by a spectrum analyzer 28, such as a microspectrometer or any suitable instrument for measuring wavelength distributions. The total blood/fluid mixture volume within the suction container 14 is measured by sensing pressure through the pressure sensor probe 20. The pressure sensor probe 20 is thus used to determine liquid height within the suction container 14 utilizing the tube 30 that is incorporated into the same probe as the optical blood sensor. The tube 30 is coupled to and thus in fluid communication with a micro-electromechanical pressure sensor 31 to measure fluid pressure within the suction canister 14 from which a volume of the fluid mixture within the suction canister 14 may be determined. If the reduced pressure in the canister becomes significant then a differential (or a second) pressure sensor can be used to measure the pressure above the fluid to provide appropriate compensation.

The blood-loss monitoring system 10 of the present invention comprises a broad-spectrum light source 24 that connects to an optical fiber 32 that extends from the light source 24 into the canister 14 and forms the distal end of the hemoglobin concentration sensor probe 16. Light that passes from the end 32' of the fiber 32 through blood in the canister loses strength due to both absorption and scattering. A second plastic optical fiber 34 having an end 34' proximate to the end 32' of the first optical fiber 32 collects the remaining light that has not been absorbed or scattered and sends it to the spectrometer 28, such as a mini-spectrometer. The output 36 of spectrometer 28 allows a display of the received intensity for all wavelengths in the visible and near infrared. Such a display is termed a transmission spectrum. Analysis of the spectrum, the collection of intensities of all wavelengths, indicates the percentage of hemoglobin mixed with other fluids as discussed herein.

The optical fibers 32 and 34 and pressure sensor tube 30 can be made sufficiently long that the instrumentation 24, 28 and 31 for generating readings from light received from the optical fibers 32 and 34 and pressure sensor tube 30 will not physically interfere with operating-room activities. In other words, the length of such components optical fibers 32 and 34 and pressure sensor tube 30 can allow for remote placement of the light source 26, spectrometer 28 and pressure sensor 31.

The light source 26, spectrometer 28 and pressure sensor 31 are electronically coupled to a processor 37. The processor 37 is configured to receive readings from the spectrometer 28 and pressure sensor 31, to determine hemoglobin concentration and fluid volume from the sensor readings and to determine blood volume in the container 14 from the determined hemoglobin concentration and fluid volume. The processor 37 is also coupled to a display 38 for displaying in real time, the volume of blood loss of the patient.

Once the processor 37 determines the concentration of hemoglobin in the container 14, the processor 37 uses this information to then determine a resulting blood loss measurement. In addition to displaying this information, the processor can be connected to and coordinate with an infusion system (known in the art) to thereby control and monitor blood infusion during a surgical procedure. Such infusion systems are employed in surgeries where blood infusion is being deployed to limit excess or insufficient blood infusion to ameliorate a patient's condition during a procedure.

Likewise, the resulting blood loss measurement may be used by the processor to calculate and control infusion volumes of crystalloid or colloid solutions to replace blood loss during surgical procedures, to thereby limit excess nor insufficient crystalloid/colloid infusions, which can be harmful to the patient.

The probe assembly 12 is inserted into a top port 40 of the operating room suction canister 14 and abuts against an inside bottom surface 42 of the suction canister. The distal end 44 of the probe assembly 12 includes a pair of legs 46 and 48 to space the distal ends of the optical fibers 32 and 34 and distal end of the pressure tube 30 from the bottom surface 42 of the canister 14. The distal ends of the optical fibers 32 and 24 are sufficiently spaced from the bottom surface of the container 14 so that tissue or other heavy particles that may sink to the bottom of the container will not interfere with the transmission of light between the ends of the optical fibers. Likewise, the legs 46 and 48 space the distal end of the pressure sensor tube 30 from the bottom surface 42 of the container 14 so that such particles do not interfere with pressure readings for volume measurements.

Figure 2:
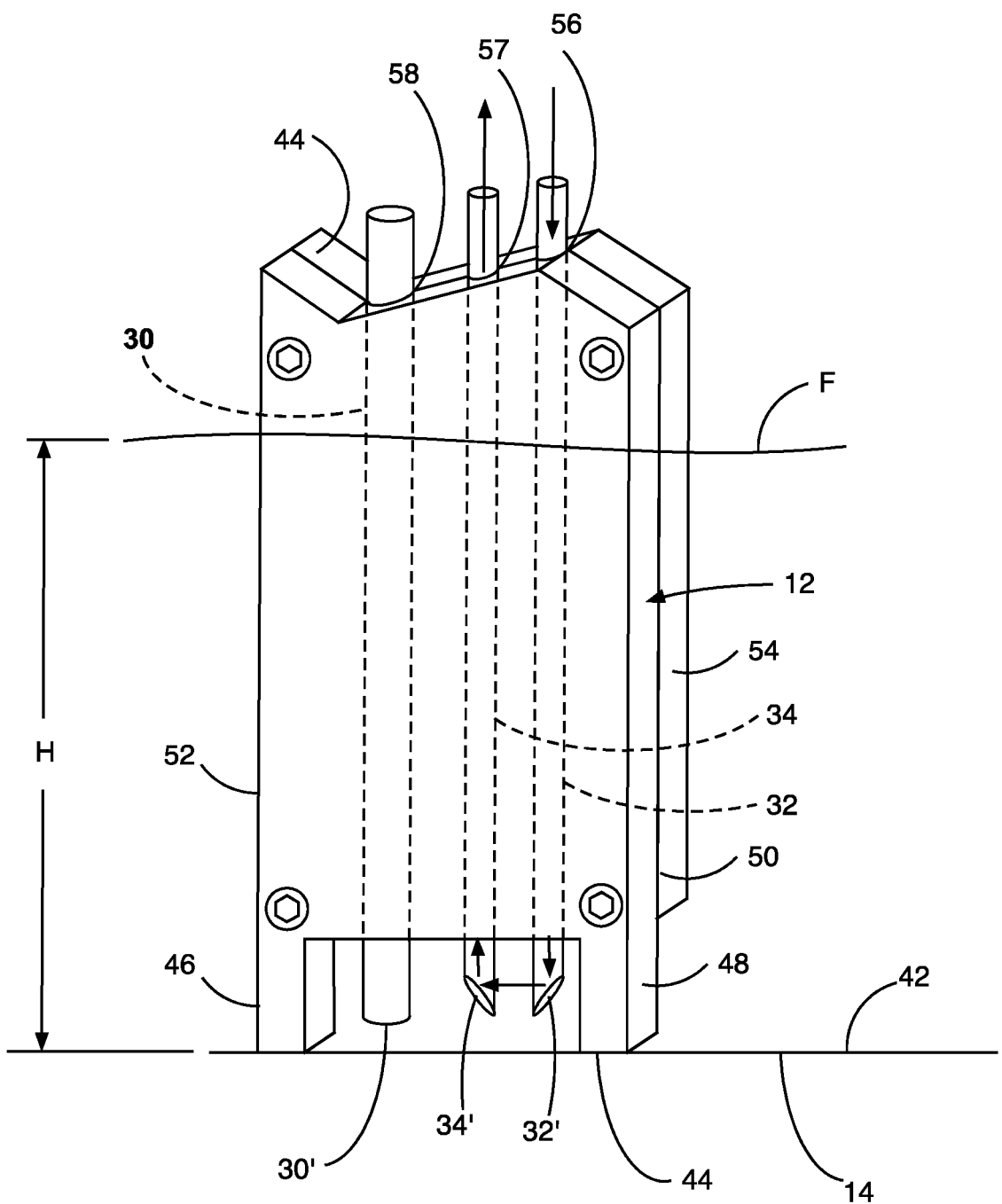
FIG. 2 is a partial front side perspective view of a hemoglobin concentration and pressure sensing probe of the blood volume measuring apparatus shown in FIG. 1.

Referring now to FIG. 2, a close up view of the distal end of the probe assembly 12 is shown. The probe assembly 12 comprises two plastic optical fibers 32 and 34 used to take a hemoglobin concentration measurement between the distal ends 32' and 34' of the optical fibers 32 and 34, respectively. The pressure tube 30, which may be comprised of a plastic tube, is used to determine the height H of fluid F in the container from which the volume of fluid in the container can be directly determined. By knowing the volume of the liquid in the canister and the hemoglobin concentration, an instantaneous amount of blood in the canister can be determined.

As previously discussed, the distal end 44 of the probe 12 is configured to be inserted in the canister and rest upon the bottom surface 42 of the canister 14. The pressure tube 30 connects back to the pressure sensor 31 (see FIG. 1). The distal ends 32' and 34' of the two optical fibers 32 and 34 are cut and polished at oppositely angled 45-degree angles. These angled surfaces cause light (indicated by arrows) to be directed from one fiber 32 through a gap between the distal ends 32' and 34' of the optical fibers 32 and 34 and into the second fiber 34, whereby the reflected light is transported up the fiber 34 and to the spectrum analyzer 28 (see FIG. 1). Fluid F that resides in the gap formed between the fibers 32 and 34 absorbs and/or scatters at least a portion of the light leaving the fiber 32 before it reaches the fiber 34. By knowing the intensity of light that is received by the fiber 34 when the container 14 is empty, a light intensity difference can be detected when fluid is present in the container 14 and the ends 32' and 34' are submerged in the fluid.

The probe assembly 12 includes a housing 50 comprised of a pair of facing housing members 52 and 54. The housing members 52 and 54 are held together with fasteners 56. The housing members 52 and 54 define a plurality of vertical channels 56, 57 and 58 therein between for housing the optical fibers 32 and 34 and pressure tube 30, respectively. The housing member 52 also includes the legs 46 and 48 to contact the bottom 42 of the container 14 when the probe assembly 12 is fully inserted into the container 14. The legs provide a space between the fiber optic ends 32' and 34' and pressure tube end 30' and the bottom 42 of the container 14 so that a sufficient volume of blood within the container and below the optical fiber ends 32' and 34' can be measured and the end of the pressure tube 30 can receive a volume of fluid such that as the level L of fluid F within the tube 30 causes an increase in air pressure within the tube 30 that can be measured with the pressure sensor 31 (see FIG. 1) in order to determine an instantaneous volume of fluid F within the container 14.

Figure 3A:
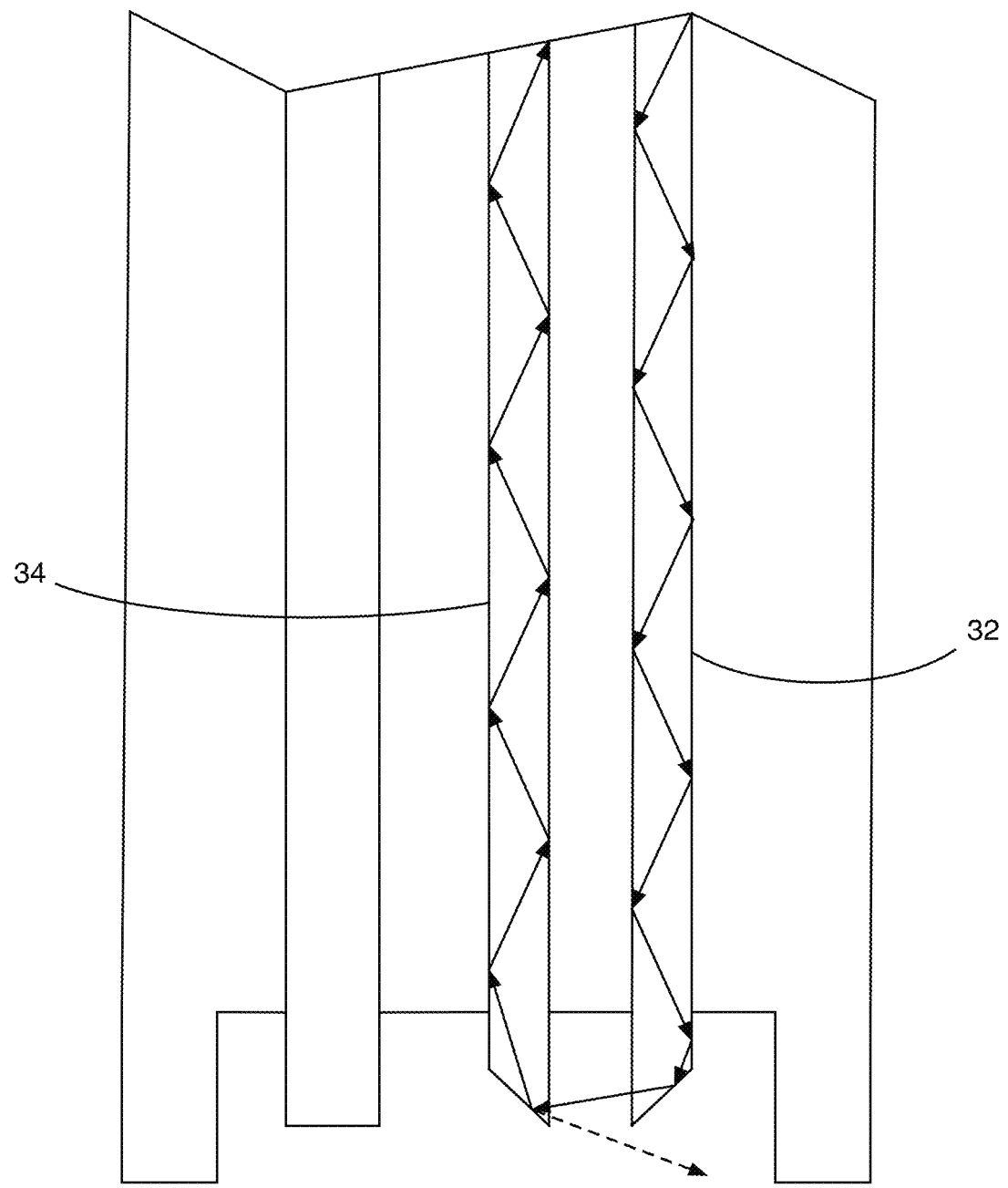
FIG. 3A is a partial front side view of the hemoglobin concentration and pressure sensing probe shown in FIG. 1 illustrating the path of a light ray.
Figure 3B:
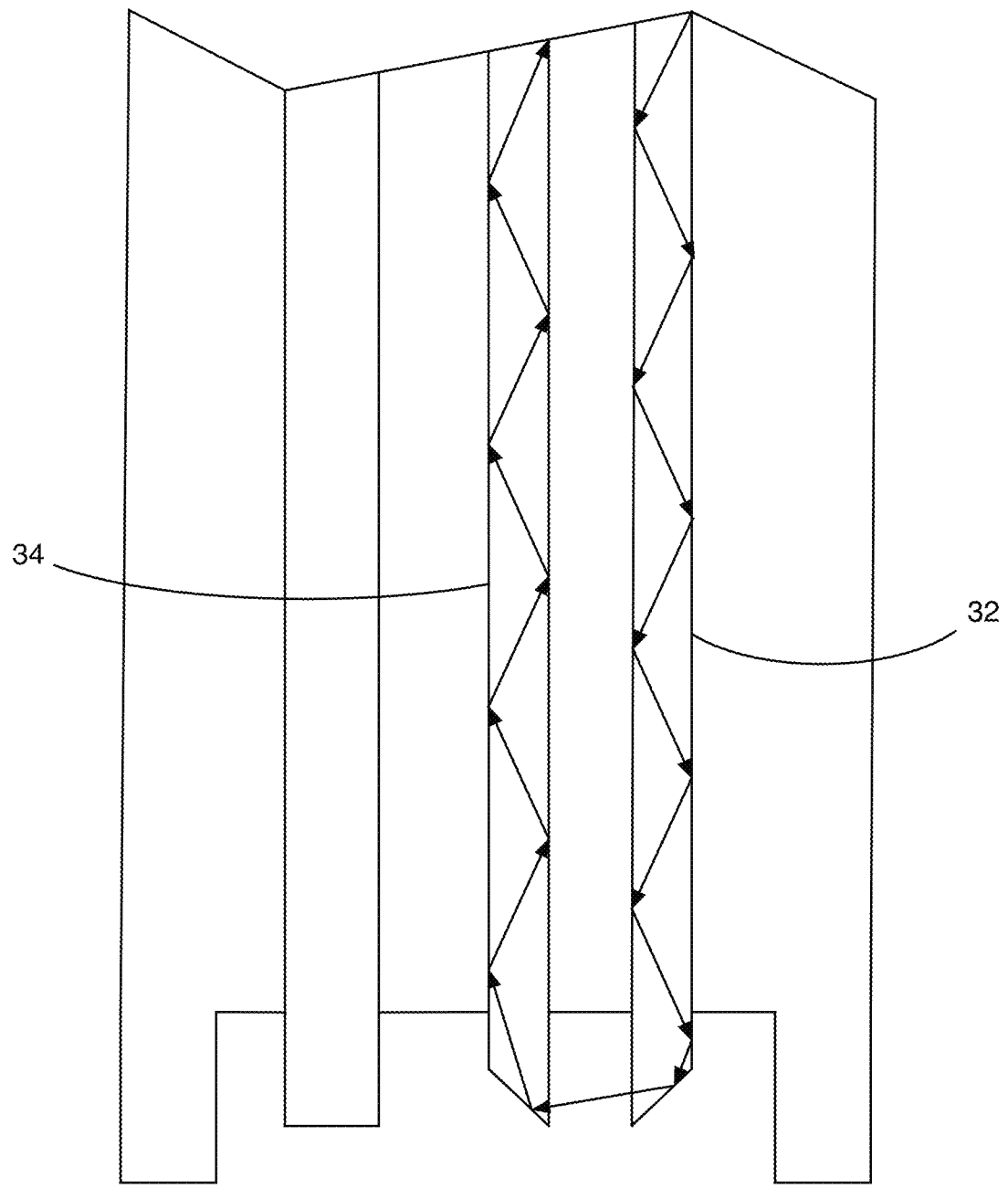
FIG. 3B is a partial front side view of the hemoglobin concentration and pressure sensing probe shown in FIG. 1 illustrating another path of a light ray.

As shown in FIGS. 3A and 3B, the 45° angled fiber pairs 32 and 34 are shown to illustrate ray-paths from one fiber to the next including reflections. The arrows depict a single transmitted light ray from one fiber 32 to the other fiber 34. It is noted, however, that other rays of light will be entering and reflecting at other angles as well. Reflections within the fiber are nearly 100% efficient if within the numerical aperture, NA. FIG. 3A illustrates the light ray in a situation where there is no fluid (other than air) surrounding the ends of the optical fibers 32 and 34. In that situation, there is some light loss that does not pass to the other optical fiber. In FIG. 3B, however, when fluid is present between the ends of the optical fibers 32 and 34, there is more transmission of light across the fluid/plastic boundary of optical fiber 34 due to index matching of the light.

The numerical aperture, NA, is determined by the following equation:

$$NA=\sqrt{n_1^2+n_2^2}$$

where $n_1$ and $n_2$ are the respective indices of refraction. In FIG. 3A, the ray of light illustrated by a dashed line indicates reflection of a fraction of the ray entering the receiving fiber 34. With no liquid in the container, this reflection is at a maximum. When fluid is added to the container, as shown in FIG. 3B, by better index matching, the amount of light lost between fibers 32 and 34 due to such reflection is less. For simplicity of explanation and illustration, it should be noted that refraction, which causes bending of light across the media boundaries at the angled ends of the fibers 32 and 34, has been ignored.

For very dilute concentrations of blood, it may be expected that the common Beer-Lambert law will hold for each ray where the transmitted light, I, by the receiver fiber is dependent on the incident light level, $I_0$; an attenuation coefficient $\alpha$ and path length, l.

$$I=I_0 e^{-\alpha l}$$

The received signal in this case will be the summation of I for each ray that crosses between the fibers. Depending on the angle, the individual path lengths will be different. As the hemoglobin concentration rises, then the attenuation coefficient will have added to it an additional complicating factor, scattering, $\mu_s$. Thus, $\alpha_{total}=\alpha+\mu_s$. Because this is not a simple scalar quantity it is difficult to model. Some rays will travel much farther in the blood due to several scattering events. In addition, the scattering effect is more or less pronounced at different wavelengths. Through testing by the applicants, $\alpha$ and $\mu_s$ work in concert to achieve blood level sensitivity according the principles of the present invention.

The mini-spectrometer 28 shown in FIG. 1 provides data files comprising intensities versus wavelength. The data is analyzed in order to determine hemoglobin concentration in the container 14. Some wavelengths of light are not absorbed significantly by blood while others are absorbed much more readily. Additionally, some wavelengths of light reflect and scatter differently from other wavelengths. In addition, the scattering characteristics versus wavelength are a function of dilution by other constituents that will be present in the container 14. For example, saline solution is often used as an irrigating medium during surgical procedures. The saline solution is removed along with blood by suction and collected in the suction canister 14. Also some wavelengths may produce fluorescence in yet other wavelengths. By illuminating the fluid within the suction canister 14 by either a broad spectrum light source or even a pair (or more) of specific wavelengths of light and the results are observed and compared with the same or other wavelengths, a ratio formed between such wavelengths can in some combinations be a function of hemoglobin concentration in the fluid contained in the suction canister. The inventors note that there are a number of possible wavelength pairs (triads, or more) from which to choose and that some wavelength pairs (triads, or more) produce better results than others. Combinations of these pairs (triads, or more) can be included for even greater accuracy and/or range.

The processor 37 receives data from the spectrum analyzer 28 and determines resultant accuracy expected for all possible wavelength pairs. The analysis performed by the processor determines the best wavelength pair from which to determine hemoglobin concentration with the least uncertainty. The spectrum analyzer groups the intensity of a continuum of wavelengths into discrete bins for analysis. From these measurement pairs of wavelengths are selected for analysis. In practice a pair should be separated by a minimum distance that insures no overlap of the intensity measurements. Here a ratio for each unique possible wavelength pair is formed. The wavelength pair and results are highly dependent on sensor design, especially the gap between the fibers. Each ratio is plotted versus hemoglobin concentration. A curve is fitted to the data. The greater the slope of this fit through the data, the greater the sensitivity. It is not only necessary to show a high sensitivity but also satisfy the other factors listed in the paragraphs herein. The greater the accuracy for a given pair of wavelengths, the better that wavelength pair is for measuring hemoglobin concentration. In order to discover the most viable pairs a three-dimensional contour plot is formed with axis 1 and axis 2 being each wavelength in a pair and axis three providing the "overall goodness of fit" as defined by the minimum uncertainty (greatest accuracy) on the independent variable (hemoglobin concentration). Peaks on the contour plot show effective wavelength pairs for accurate measurement. That is, at such pairs the ratio is strongly hemoglobin concentration dependent with minimal uncertainty and therefore greatest accuracy. These results can also be displayed with a spreadsheet that is easy to use which will produce the results of interest. The optimal wavelength pair(s) is unique to the particular probe design and construction, since different sensor designs may have distinctive absorption paths. It should also be noted that, for sources that are light emitting diodes (LEDs), since an LED light source is not a pure line but a Gaussian distribution, it is straightforward to use a Gaussian-weighted average around the peak wavelength in calculating the result. This value can be set over any range. A useful value generally is about 50 nm. Subsequently, after LEDs or other light sources are selected, the actual wavelength distributions may be used for modeling and testing. Once a wavelength pair(s) is selected, the above analysis is reduced to the calibration obtained for that pair. The final product would only need the intensities of the desired wavelengths and the fixed calibration obtained.

Since the excitation light intensity can vary over time, measuring absolute intensities does not necessarily produce consistent results. However, a good assumption is that only the overall light intensity varies and the relative individual wavelength intensities stay consistent relative each other. Therefore, by generating a ratio of the intensities the overall amplitude cancels out and the result is a unique number that is independent of the overall intensity.

For a given wavelength pair the ratio is computed and linked to the hemoglobin content of the sample. When enough samples are gathered that cover a desired hemoglobin concentration range, the statistically acceptable results can be plotted with the ratio on the ordinate and the hemoglobin content on the abscissa. A curve is generated that best fits these points and analyzed with respect to the best conditions of fit as set forth herein. This process is repeated for all unique wavelength pairs possible and the wavelength pairs that produce the best results are utilized.

To test the system for measuring blood loss according to the principles of the present invention, human blood from a blood bank contained in a single pouch was used in sample sets to maintain the relative hemoglobin concentration of the 100% sample. Each sample was precisely measured and diluted with saline to form a specific hemoglobin concentration from between 5% to 100%. Each sample was also measured with a HEMOCUE hemoglobin analyzer to confirm each blood sample's hemoglobin concentration and to provide an absolute reference. The system for measuring blood loss according to the principles of the present invention was able to determine the relative dilution of each sample.

As such, the system for measuring blood loss according to the principles of the present invention can accurately provide the concentration of hemoglobin in a suction canister containing blood, various other fluids (such as saline) and other constituents (such as tissue and/or bone fragments) in the suction canister during a medical procedure (such as surgery). In order to more accurately provide to medical personnel a more precisely calculated blood loss volume of the patient resulting from the detected hemoglobin concentration of the fluid in the canister, the initial hemoglobin concentration of the patient must be known. Once the hemoglobin concentration of the fluid in the canister is measured, the volume of fluid in the canister is known (by determining volume by using the pressure sensor as described herein, by using light sensors as described herein, by video detection, by visual inspection or other means), and the initial or real time hemoglobin concentration of the patient's blood before being diluted by saline and/or other fluids and constituents in the canister are known, the system for measuring blood loss according to the principles of the present invention can determine total blood loss in real time. The patient's hemoglobin concentration can be provided to the system for purposes of calculating blood loss in various ways. First, by making an assumption that the patient's blood hemoglobin concentration remains constant throughout the surgery, a pre-op hemoglobin concentration measurement can be taken before surgery. This is a reasonable assumption for surgeries not lasting many hours since hemoglobin concentration tends to remain relatively constant for short surgeries. Second, an estimate of how much of the patient's hemoglobin concentration is changing during the surgery, for example based on IV administration of saline or other fluids to the patient during surgery by which the system decreases or increases the hemoglobin concentration from an initial hemoglobin concentration according to curves that have been generated based on historical data of hemoglobin concentrations of patients compared to volume of saline and/or other fluids administered during surgery. Third, the patient's actual hemoglobin concentration could be measured throughout the surgery, either invasively or noninvasively. The measured hemoglobin concentration is then input into the system in real time as part of the real time blood loss volume calculation provided by the system of the present invention. Thus, by knowing the blood source concentration, the absolute hemoglobin concentration can accordingly be accurately obtained.

Once a wavelength pair(s) is selected, the above analysis is reduced to the calibration obtained for that pair. The blood loss measuring system of the present invention would then only need the intensities of the desired wavelengths and the fixed calibration obtained to determine hemoglobin concentration within the suction canister.

One method of calculating an estimated blood loss (EBL) is set forth below. The method uses total Hgb mass (g) lost in canister as a fraction of original Hgb mass in patient. First, the total Hgb mass (g) in the canister is calculated. After adjustment for units, Volume$_c$ (cc)/100×Hgb$_c$ (g)=total Hgb mass (g) in canister Next, the preop Hgb mass (g) of patient is calculated.

TBV=total blood volume

After adjustment for units,

TBV (cc)/100×preop pt Hgb (g)=total preop Hgb mass (g) of patient

Next, the percent of Hgb mass (g) lost in canister is calculated.

% Hgb mass lost (g)=% blood lost from preop TBV=EBL (cc)

The most accurate way to assess TBV is to use the Nadler's equation.

| Patient | Total Blood Volume (mL) |
|---------|-------------------------|
| Male    | $(0.006012 \times H^3/(14.6 \times W) + 604$ |
| Female  | $(0.005835 \times H^3)/(15 \times W) + 183$ | where H=height in inches and W=weight in pounds.

Another way to estimate Total Blood Volumes is based on Gilcher's Rule of Five.

Blood Volume (mL/kg of Body Weight)

| Patient | Obese | Thin | Normal | Muscular |
|---------|-------|------|--------|----------|
| Male    | 60    | 65   | 70     | 75       |
| Female  | 55    | 60   | 65     | 70       |
| Infant/Child | — | —   | 80/70  | —        |

The reason for the difference is secondary to the difference in vascularity between adipose tissue and muscle tissue. For very obese patients the total blood volume can be estimated by using the lean body weight plus 20%.

For pediatric patients, the Total Blood Volume can be estimated as follows:

| Age group | Approximate Blood Volume (mL/kg) |
|-----------|----------------------------------|
| Premature infant at birth | 90-105 |
| Term newborn infant | 80-90 |
| Children (<3 months) | 70-75 |
| Adolescents | |
| Male | 70 |
| Female | 65 |

The blood loss measuring system 10 of the present invention may be embodied in a number of related but different manifestations. For example, using data acquired by a broad-spectrum light source and a mini-spectrometer, hemoglobin concentration can be determined. Utilizing such results to determine one or more optimal wavelength pairs, two (or more) LED light sources that closely match at least one of the optimal wavelength pairs can be selected. Utilizing a broadband light source and spectrometer provides the greatest accuracy at the greatest expense. The LEDs that produce light of the optimal wavelength(s) can replace the broadband light source and eliminate the need for a spectrometer greatly reducing cost.

In order to determine the best or optimal wavelengths for a given probe design, the following approach may be taken:
1) By using a ratio approach according to the present invention, light source intensity variations are eliminated. It is this ratio that is used as the input to the resultant algorithm that produces the percent hemoglobin concentration.

$$\% \ Concentration = f(r) = a \cdot r^2 + b \cdot r + c$$

where:

$$r = \frac{I_1(IntensityOfWavelength \#1)}{I_0(IntensityOfWavelength \#0)}$$

2) A necessary constraint is that there be a monotonic relationship of the particular wavelength ratio pair to the hemoglobin concentration over the range of interest. (If it is not monotonic then more than one answer is available for a given input.)
3) A further requirement is that the selected wavelength ratios be most sensitive throughout the range of the resultant hemoglobin concentration. That is, the slope of the line of the ratio versus the concentration is the largest obtainable. This insures a small uncertainty in the percentage of hemoglobin calculated.
4) In addition, the measured data, to have the highest accuracy, must have the smallest standard deviation of fit to the resultant empirical function, whether a polynomial, a spline, a piecewise fit, or other function, which relates the ratio of the selected wavelength pairs chosen to determine the hemoglobin concentration.
5) Also of concern is the variation of fit (accuracy) over the region of interest to account for slight variations in the manufacturing of the sensor probes. That is, small variations in wavelengths of interest and probe design should produce the same result.
6) Fitting the measured ratio (y) to the percent hemoglobin concentration (x) for quadratics and cubics yields very good fits for certain pairs of wavelengths. It is important to select the optimum pair(s) as some available pairs do not show any or much sensitivity to concentration.
7) By using more than one pair of wavelengths, multiple measurements can be made simultaneously and averaged together for even more accurate results and less sensitivity to probe design. Some pairs could share wavelengths (e.g., 3 wavelengths could produce up to 3 pairs to analyze).

When the "best" or "optimal" wavelengths for a given probe design are determined, a curve fit equation can be derived for the actual data. If individual light sources are used (e.g. LEDs) then they may be time multiplexed requiring only a single photodetector. Also their relative amplitudes can be tracked over time by measuring them before any fluid enters the canister, which would then be used to compensate any long term drift. After a few minutes the LED's should achieve thermal stabilization and remain constant for extended periods of time.

Figure 4:
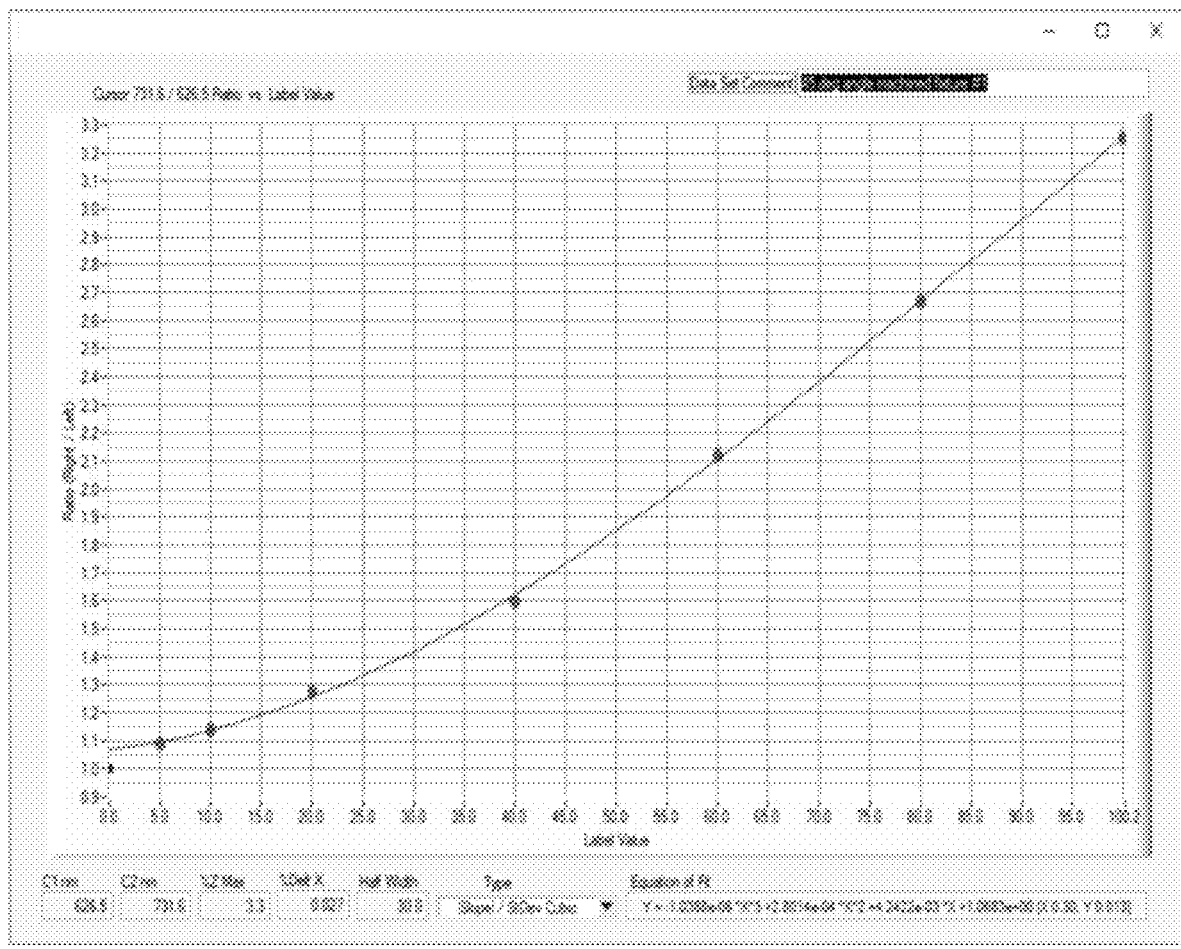
FIG. 4 is a graph illustrating signal in form of ratios versus concentration in percentages in accordance with the principles of the present invention.

As shown in FIG. 4, the actual data matches the derived equation. The graph in FIG. 4 compares results of a single test using the probe assembly illustrated in FIG. 1 with a cubic fit to the results for a pair of wavelengths with a 0.3% sigma (standard deviation) fit on hemoglobin concentration for the above requirements. To determine the ratios that satisfy the above criteria, a full spectrum is measured at each concentration and all combinations of wavelengths in each spectrum are analyzed. Those ratios that best meet the criteria are then used in the final analysis. FIG. 4 illustrates a plot of signal (in form of ratio) to concentration (%). Parameters of interest are listed at the bottom of the figure and equation of fit is in lower right of figure.

If the above criteria cannot be met in total or are not accurate enough for a single pair, then regions of concentration can be identified that do fit the above criteria and different wavelength ratios can then be used for each region. That is, each ratio pair would be valid for restricted regions of concentration, but when used in combination would then define the entire region of interest.

Other items of interest (urine, Heparin, etc.) might also be measured in parallel by using additional ratios.

Figure 5:
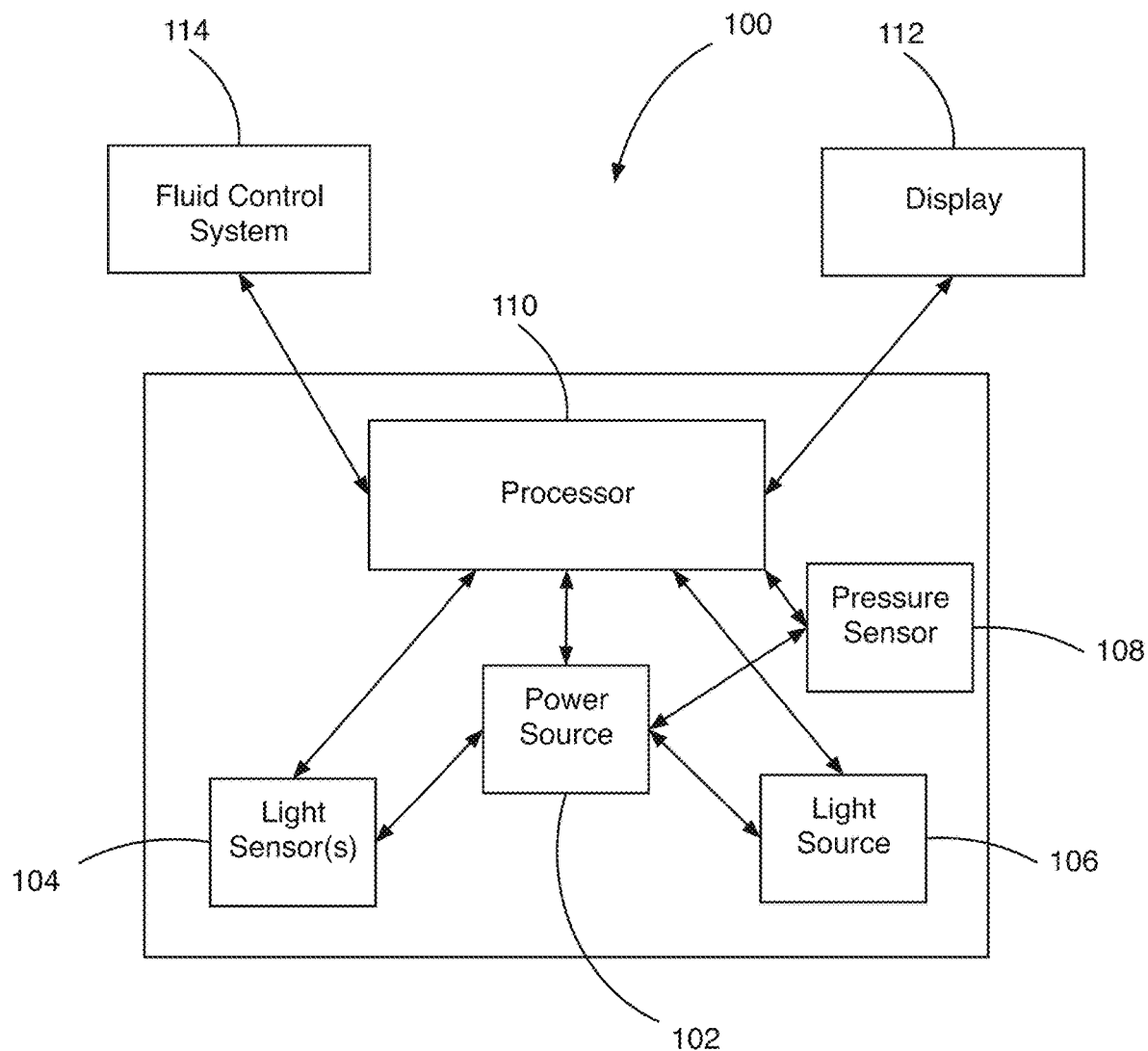
FIG. 5 is a schematic block diagram of various components of a blood volume measuring apparatus in accordance with the principles of the present invention.

As shown in FIG. 5, in a further aspect, the blood measurement device 100 can comprise a power source 102 positioned in operative communication with one or more light sensors 104, such as a photodetector, a light source 106 and a processor 110. The power source 102 can be positioned in operative communication with the light source 106, light sensor 104 and processor 110 through conventional wiring 72. The power source 102 can be any conventional power source as is known in the art. For example, the power source 102 may comprise a battery. In other exemplary aspects, it is contemplated that the power source can comprise a DC power source. In still other exemplary aspects, it is contemplated that the power source can comprise an AC power source. The processor 110, includes a processor chip such as a microprocessor, and is operably coupled to the light source 106, light sensor 104 and pressure sensor 108. The light sensor 104 and pressure sensor 108 send signals to the processor, which signals may comprise analog or digital information to indicate the amount of light being detected by the light sensor 104 and pressure detected by the pressure sensor 108. The information is then used by the processor 110 to determine a hemoglobin concentration in the suction canister thereby indicated the amount of blood loss of the patient. The quantity of blood loss can then be displayed on a display 112 that is also operably coupled to the processor 110. In addition, the processor 110 may be operably coupled to one or more fluid control systems 114 such as an IV drip system to increase fluid to the patient depending on the amount of fluid loss of the patient or to an blood transfusion system to increase blood flow to the patient to account for any blood loss detected by the blood loss measuring system 100 of the present invention.

In use, and as schematically depicted in FIG. 5, it is contemplated that the blood loss measuring system 100 can be configured to create a feedback loop at any given time between the calculated patient hemoglobin concentration and the hemoglobin concentration and volume of the sample fluid, thereby resulting in a continuous display of estimated patient blood loss. After the blood loss measuring system 100 calculates the estimated blood loss and the updated patient hemoglobin concentration based on the data output from the light sensors as disclosed herein, the results can be transmitted to a memory and/or display 112 that are in communication with the processor 110.

Figure 6:
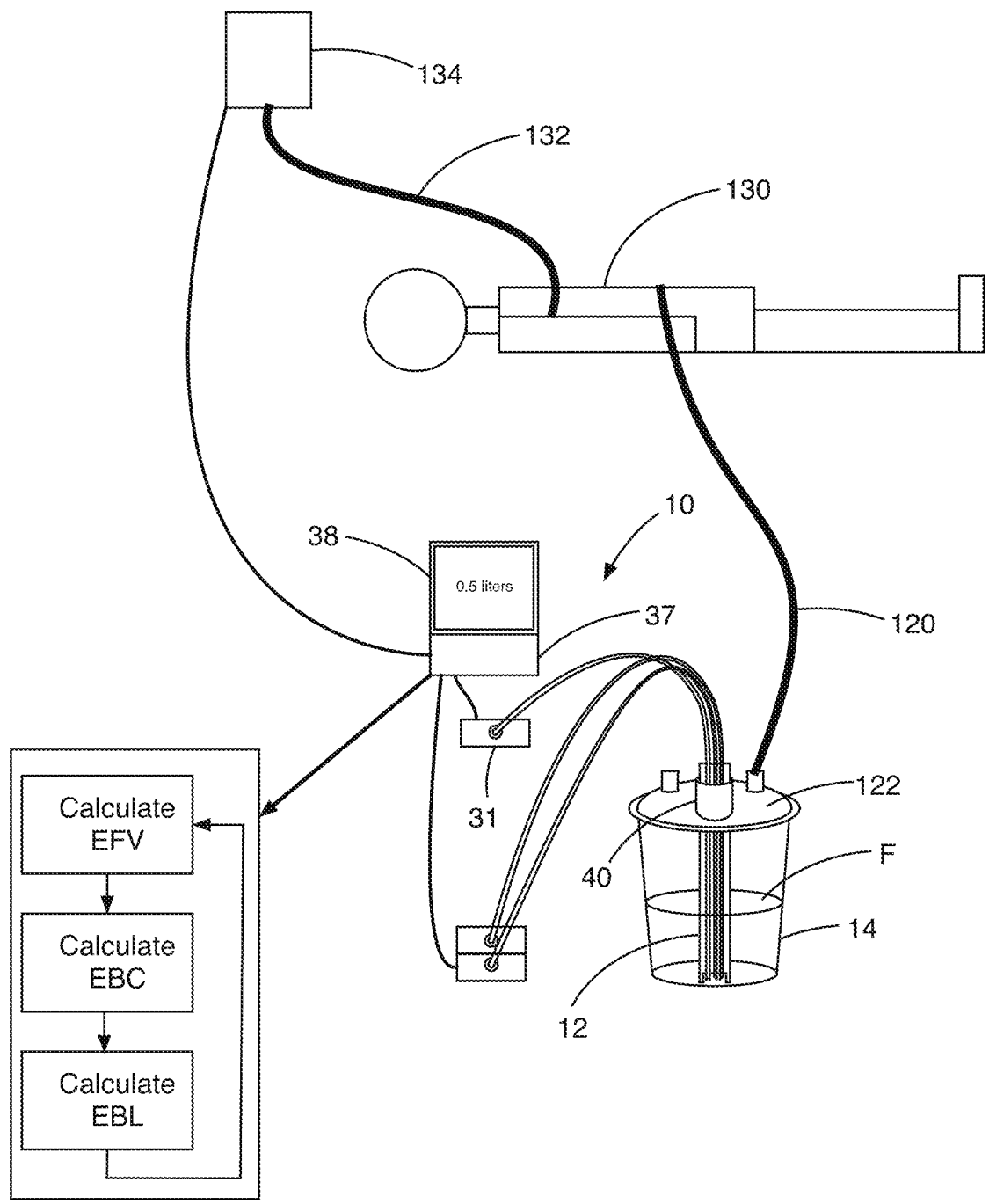
FIG. 6 is a front side view of the blood volume measuring apparatus of FIG. 1 when connected to a patient in accordance with the principles of the present invention.

As shown in FIG. 6, the blood loss measuring system 10 comprises the blood measurement probe 12 and a container 14, such as, for example and without limitation, a suction canister 20. Although described herein as a suction canister, it is contemplated that the container can be any conventional container that is configured to receive a fluid sample F. For example, in exemplary aspects, it is contemplated that the container can be a cell saver, which is configured to clean a fluid sample to permit delivery of the fluid sample to a patient. It is contemplated that the suction canister 14 can be configured for operative coupling to one or more sections of suction tubing 120 as are conventionally used during surgical procedures to facilitate transport of bodily fluids and/or irrigation fluids to the suction canister 14. It is further contemplated that the suction canister 14 can have any conventional shape, including, for example and without limitation, a substantially cylindrical shape. It is still further contemplated the suction canister 14 can have any selected dimensions. In exemplary aspects, it is contemplated that the suction canister 140 can have a volume ranging from about 0.5 liter to about 5 liters. Fluid from the suction tubing 120 is collected in the suction canister 14. The patient 130 may also be receiving IV fluids and/or blood transfusion through other tubing 132 from and IV or blood transfusion system 134.

As fluid F is collected in the canister 14, the blood loss measuring system of the present invention determines the volume of fluid F in the canister 14 and the hemoglobin concentration in the fluid F. This information is received by the processor 37. The processor 37 calculates the estimated fluid volume (EFV) in the canister 14 from either the pressure data received from the pressure sensor 31 or from an optical signal analysis of measured optical wavelength bands that, independent or those relevant to or required for the hemoglobin concentration, have signals that change appropriately to different fluid levels. This optical analysis would determine the depth of the fluid in the canister or other blood container. The wavelength bands used could be measured as transmissions through the fluid or, more likely, light returning from the source that is affected by the properties of the interface between fluid and air. Simultaneously, or near simultaneously, but in real time, the processor 37 calculates the estimated hemoglobin blood concentration (EBC) from the concentration of hemoglobin detected in the fluid F. Knowing the EFV and EBC in the canister 14, the processor 37 then determines the estimated blood volume (EBV) contained within the canister 14. This information is then displayed in real time on the display 38. The display 38 may also show the EFV in real time so that medical personnel can compare the EFV with the actual fluid volume in the canister 14 that can be visually seen by such personnel by comparing the volume of fluid F in the canister 14 with volume indication markings on the canister 14. If there is an unexpected discrepancy between the EFV and actual fluid volume, the system 10 allows personnel the option to adjust the detected volume level in the system so as to obtain more accurate results of the EBV. That is, when the EFV is overridden, the processor 37 will recalculate the EBV based on the new EFV.

Figure 7:
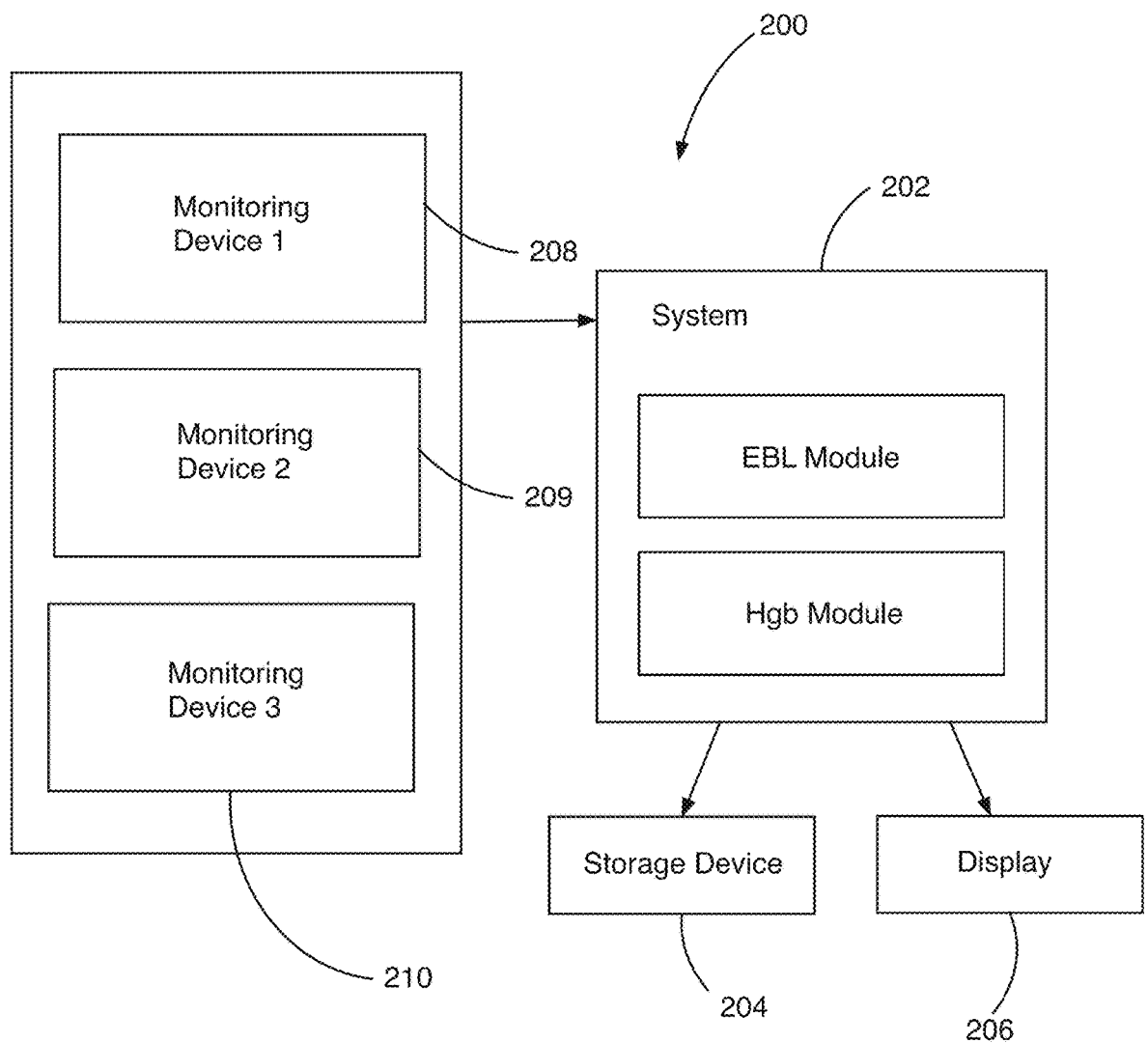
FIG. 7 is a schematic block diagram of various components of a blood volume measuring apparatus in accordance with the principles of the present invention.

As shown in FIG. 7, a blood loss measuring system 200 of the present invention may comprise a processor 202 as is conventionally known in the art. The processor 202 can be provided in the form of a computer, and the processor 202 can be in operative communication with memory 204 (or other storage device) and/or a display 206 as are known in the art. It is contemplated that the memory 204 can optionally store software that, when executed, is configured to perform one or more of the steps and calculations disclosed herein. It is further contemplated that the memory 204 can store historical information related to the hemoglobin concentration and/or blood loss of particular patients. In exemplary optional aspects, the processor 202 can be provided as a microcontroller that is secured to or housed within a portion of the device 200. As further disclosed herein, the processor 202 can comprise one or more modules for determining at least one of the estimated blood loss (EBL) of the subject, the hemoglobin concentration (Hgb) of the fluid sample, and the volume of the fluid sample. In exemplary aspects, the processor 202 can be configured to receive one or more inputs from a user or a memory indicative of at least one of a previously measured EBL of the subject, a previously measured hemoglobin concentration of the fluid sample, a previously measured volume of the fluid sample, a volume of the container (e.g., canister) in which the fluid sample is positioned, the rate of IV fluid (or other fluid) administration, the sex of the subject, the weight of the subject, the age of the subject, and the like. Optionally, it is contemplated that the processor 202 can be positioned in operative communication with a user interface that is configured to receive the one or more inputs from a user. In exemplary aspects, the display and/or user interface can be secured to or defined thereon a portion of the device 200.

The processor 202 may also be operably coupled to one or more monitoring devices 208, 209 and 210. The monitoring devices may include one or more external patient monitoring devices that may be related to the blood levels of the patient that may further be used to indicate accuracy of measurement of the blood loss measuring system of the present invention. The monitoring devices may also include pressure monitoring and blood/hemoglobin concentration of the fluid contained within the suction canister as herein described. Thus, the system 200 of the present invention may be expanded to include other monitoring devices, whether now known in the art or that may become known in the future.

For example, the system 200 can further comprise a drip counter configured for communication with an intravenous (IV) fluid delivery element, such as, for example and without limitation, an N bag as is known in the art. In this aspect, the drip counter can be configured to produce a volume signal indicative of the volume of IV fluid dispensed from the IV fluid delivery element and/or a delivery rate signal indicative of the rate at which IV fluid is dispensed from the IV fluid delivery element. It is contemplated that the drip counter can be positioned in operative communication with the processor 202 such that the processor is configured to receive the volume signal and/or the delivery rate signal. Alternatively, the volume and/or rate information can be entered manually by a user of the system 200.

In further exemplary aspects, it is contemplated that the blood measurement system can optionally comprise a plurality of blood measurement devices that have a common processor or, alternatively, that have discrete processors that are in operative communication with each other. In these aspects, it is further contemplated that the blood measurement system can comprise a plurality of containers (e.g., a plurality of suction canisters 14), with a blood measurement device being configured for selective positioning relative to a respective container. It is contemplated that such a configuration can permit determination of comprehensive blood loss information in circumstances when more than one container is used to collect fluids during a single medical procedure.

Referring again to FIG. 6, in other exemplary aspects, it is contemplated that a lid 122 of the canister 14 can define one or more receptacles 40 that are configured to receive at least a portion of the probe 12. The lid 122 is configured to enclose a top opening of the canister 14. In these aspects, it is contemplated that the lid of the canister 14 can define at least one opening configured to receive one or more portions of the blood loss measuring device 10, including, for example and without limitation, the probe 12 that houses the optical fibers and pressures sensor tube.

In one aspect, the suction canister 14 can have a central axis that, during use, is generally axially aligned with the vertical axis. In one aspect, the suction canister 14 can have a wall with an internal surface and an external surface. The internal surface of the suction canister 14 can define an interior space of the suction canister 14. It is contemplated that the interior space of the suction canister 14 can be configured to receive the fluid sample F. In exemplary aspects, the suction canister 14 can comprise conventional plastic materials, including, for example and without, transparent plastic materials. In further exemplary aspects, it is contemplated that the suction canister 14 can be provided with volume measurement lines and other measurement lines and markings as are conventionally known in the art.

Optionally, it is contemplated that the light sensor optical fibers and pressure sensor tube can be selectively operatively coupled to a wall of the suction canister 14. However, in some aspects, it is contemplated that the light sensor optical fibers and pressure sensor tube can optionally be positioned within a central portion of the interior space of the suction canister 14 (and radially spaced from the wall of the suction canister 14).

In other exemplary aspects, it is contemplated that one or more components of the blood measuring device 10 can be integrally formed with the canister 14. For example, in some aspects, the probe 12 can be integrally formed with the wall of the canister 14. In further exemplary aspects, it is contemplated that at least a portion of the optical fibers disclosed herein can be integrally formed (for example, embedded within) the wall, bottom portion, and/or lid of the canister 14.

It is also contemplated that the blood measurement system 10 can comprise a stirrer positioned within the interior space 25 of the suction canister 20. In exemplary aspects, the stirrer can be a magnetic stirrer as is known in the art. However, it is contemplated that the stirrer can be any conventional stirrer as is known in the art. It is further contemplated that the stirrer can be configured for selective activation. In exemplary aspects, it is contemplated that the stirrer can be positioned proximate the bottom surface of the suction canister 14.

In use, the disclosed blood loss measuring system of the present invention can be used to measure the amount of blood within a fluid sample. In exemplary aspects, the blood loss measuring system can be used to measure the blood loss of a subject during a medical procedure, such as, for example and without limitation, a surgical procedure. As set forth herein, it is contemplated that the blood loss measuring system can be configured to repeatedly measure the hemoglobin concentration of the fluid sample within a suction canister, as well as the volume of the sample fluid within the suction canister. Throughout the medical procedure, it is contemplated that the blood loss measuring system can be configured to export these measurements to the processor 202, which can use the measurements, along with the updated concentration of the subject's hemoglobin concentration, to calculate the volume of blood in the suction container. Thus, a method of measuring the amount of blood of a subject within a fluid sample (e.g., determining the blood loss of the subject) can comprise operatively positioning the blood measurement device relative to the fluid sample and using the blood measurement device to determine the concentration of hemoglobin within the fluid sample. More specifically, the method can comprise positioning the light source and the at least one light sensor in an operative position relative to the fluid sample. With the light source and the light sensor positioned in the operative position, the method can further comprise selectively activating the light source to sequentially generate light at the first and second wavelengths. The method can further comprise receiving the transmitted light using the at least one light sensor. The method can still further comprise, through the processor, receiving the first and second output signals of the at least one light sensor and determining the hemoglobin concentration within the fluid sample. In further exemplary aspects, the method can comprise, through the processor, determining the volume of blood within the fluid sample. In still further exemplary aspects, the method can comprise, through the processor, determining the volume of the fluid sample. Alternatively, it is contemplated that the method can comprise, through the processor, receiving an input indicative of the volume of the fluid sample. In further exemplary aspects, the method can optionally comprise, through the processor, receiving an input indicative of a starting (or other previously measured) hemoglobin concentration of the subject.

In exemplary aspects, the hemoglobin concentration of the fluid sample within the suction container can be measured through one or more hemoglobinometry techniques as are known in the art. Generally, these known color or light-intensity matching techniques can be used to measure the concentration of methemoglobin or sulphemoglobin, which provide an indication of the overall hemoglobin concentration of the fluid sample within the suction canister. Thus, in various aspects, the method of measuring the amount of blood of a subject within a fluid sample (e.g., determining the blood loss of the subject) can optionally comprise administering one or more reagents to the fluid sample. In these aspects, the one or more reagents can be configured to convert hemoglobin within the fluid sample into one of methemoglobin and sulphemoglobin. In exemplary aspects, the fluid sample can optionally be positioned within a suction canister as disclosed herein, and the one or more reagents can be added to the suction canister. In some exemplary aspects, it is contemplated that the one or more reagents (and/or a solution containing such reagents) can be administered to the internal surface of the suction canister. In other exemplary aspects, it is contemplated that the one or more reagents can be added to the suction canister 14 (or other container) before the fluid sample is received within the suction canister (or other container). In further exemplary aspects, it is contemplated that the one or more reagents can be applied to selected surfaces of the blood measurement device that are configured for positioning within the fluid sample. In these aspects, it is contemplated that the one or more reagents can be configured to circulate within the fluid sample following contact between the selected surfaces of the blood measurement device 10 and the fluid sample. In some aspects, the reagents (and/or the solution containing the reagents) can be allowed to air-dry. Alternatively, in other aspects, the reagents (and/or a solution containing such reagents) can be provided at a predetermined concentration such that dilution of the reagents and/or solution by the fluid sample can yield a desired reagent concentration.

An exemplary method for measuring the methemoglobin concentration within the fluid sample comprises the use of hem iglobincyanide (HiCN; cyanmethamoglobin) as a reagent. The use of hem iglobincyanide as a reagent is described in Zijlstra W G, Van Kampen E. Standardization of hemoglobinometry. I. The extinction coefficient of hemiglobincyanide. Clin Chim Acta. 1960 September; 5:719-26, which is incorporated herein by reference in its entirety. Alternatively, in one exemplary aspect, the reagent can comprise sodium azide or sodium lauryl sulphate, which convert the hemoglobin to azidmethemiglobin and hem iglobinsulphate, respectively. Exemplary methods of measuring hemoglobin within the blood using sodium azide are described in Vanzetti G. An azide-methemoglobin method for hemoglobin determination in blood. J Lab Clin Med. 1966 January; 67(1): 116-26, which is hereby incorporated herein by reference in its entirety. Exemplary methods of measuring hemoglobin within the blood using sodium lauryl sulphate are described in Oshiro I, Takenaka T, Maeda J. New method for hemoglobin determination by using sodium lauryl sulfate (SLS). Clin Biochem. 1982 April; 15(2):83-8, and in Lewis S M, Garvey B, Manning R, Sharp S A, Wardle J. Lauryl sulphate haemoglobin: a non-hazardous substitute for HiCN in haemoglobinometry. Clin Lab Haematol. 1991; 13(3):279-90, both of which are hereby incorporated herein by reference in their entirety. Optionally, in some aspects, it is contemplated that one or more lysing agents can be added to the solvent. Exemplary lysing agents can be selected from the group consisting of desoxycholate, quaternary ammonium salts, and quaternary ammonium surfactants, such as, for example and without limitation, anionic, non-ionic, zwitterionic, and cationic surfactants. In one exemplary aspect, the following compositions can be added per liter of solvent: 40 g sodium desoxycholate (to lyse the cells within the fluid sample); 20 g sodium nitrite (to convert the hemoblogin iron from ferrous to ferric state); and 18 g sodium azide (to form azidmethemoglobin).

Optionally, in various exemplary aspects, the method of measuring the amount of blood of a subject within the fluid sample can further comprise delivering an anti-coagulant to the fluid sample. In these aspects, it is contemplated that the method of measuring the amount of blood of the subject within the fluid sample can comprise delivering a desired amount of anti-coagulant for each liter of fluid sample that is collected within the suction canister or other container. In exemplary aspects, the anti-coagulant can be Heparin. In these aspects, it is contemplated that the method of measuring the amount of blood of the subject within the fluid sample can comprise delivering a selected number of units of Heparin for each liter of fluid sample that is collected within the suction canister 20 or other container. For example, it is contemplated that that the selected number of units of Heparin can be about 20,000 units of Heparin per liter of fluid sample. However, it is contemplated that any conventional anti-coagulant drug can be delivered in a selected quantity relative to the volume of the fluid sample. For example, it is contemplated that the anti-coagulant can be selected from the group consisting of Ethylenediaminetetraacetic acid (EDTA) and Citrate.

Optionally, in some applications, it is contemplated that a plurality of anti-coagulants can be delivered to the fluid sample. In further exemplary aspects, it is contemplated that the anticoagulant or plurality of anti-coagulants can be provided to the fluid sample in any form, including, for example and without limitation, liquid or solid forms. Typically, it is contemplated that the anti-coagulant(s) can be delivered using a syringe as is conventional in the art. However, it is contemplated that any suitable delivery method can be used. In one exemplary aspect, it is contemplated that a solid form of the anti-coagulant can be fixedly coupled to the internal surface of a suction canister such that the anti-coagulant contacts the fluid sample as it fills up the suction canister. In another exemplary aspect, it is contemplated that a solid form of the anti-coagulant can be fixedly coupled to selected portions of a base element 80 as disclosed herein such that the base element can be selectively inserted within the fluid sample to provide the anti-coagulant to the fluid sample.

In methods in which anti-coagulants are not provided to the fluid sample, it is contemplated that absorbance data obtained when the fluid sample first enters the canister or other container should be used in determining the hemoglobin concentration, whereas the absorbance data obtained following coagulation of the blood within the fluid sample should be disregarded. Thus, it is contemplated that the processor can be configured to disregard absorbance data obtained following coagulation of blood within the fluid sample. Alternatively, the method can comprise inserting the light source and the at least one light sensor into the fluid sample before coagulation of the blood within the fluid sample has occurred and removing the light source and the at least one light sensor from the fluid sample and/or ceasing activation of the light source and at least one light sensor after coagulation of the blood within the fluid sample has occurred.

While some prior art devices utilize the difference in absorption by the blood of two different wavelengths, the present invention is novel and nonobvious because it utilizes multiple wavelengths across a broad spectral range and uses these in a manner that allows for minimizing uncertainty and allowing for variances in sensor construction and other situations that may be encountered. Utilizing a spectrum analyzer allows for variation in light sources to be compensated.

While LEDs may vary in wavelength, as manufacturers specifications show, the spectrum analyzer can account for such variations. It is also contemplated that when selecting LEDs of specific wavelengths, a spectrum analyzer could by utilized in advance to determine the actual wavelength of light being emitted by a particular LED and then accounting for the actual frequency of light being emitted by the LEDs.

The present invention provides a region of absorption of light that is optically engineered in a way different than any prior art absorption based sensors. By cutting and polishing the end of the fibers at a 45 degree angle and orienting them as in shown in FIGS. 1, 2, 3A and 3B, light is captured efficiently and the curvature of the fiber, which relates to optical power, results in an efficient light capturing arrangement. In addition, the optical fibers of the present invention efficiently capture light that may undergo a number of scattering events. Thus, there is not a single absorption path length to which to apply Beer's law, but a distribution of path lengths. As such, the fiber optic configuration of the present invention provides effective blood absorption measurements and has been empirically shown to do so.

Thus the present invention provides a sensor, such as a MEMs sensor, for measuring pressure (or differential pressure) that is integrated into a package with an optical system for measuring hemoglobin concentration, or an optical measurement that determines fluid level. The results are combined to determine the amount of blood loss. An optical absorption approach involving the entire visible spectrum enables measurements at varying concentrations in saline solution. This is achieved using an inexpensive probe assembly. The probe assembly may be entirely comprised of plastic components that are inexpensive to manufacture and can be discarded after coming into contact with blood in the canister. Thus, the probe assembly can be made to be disposable. The plastic optical fibers transport interrogation light and emission light to and from the operating room canister. The single zone probe is constructed from PMMA and plastic optical fibers, thereby being inexpensive and disposable. The mathematical solution of the present invention in conjunction with a spectrum analyzer provides a 3-dimensional mathematical method for hemoglobin concentration measurement and determination. In addition, the present invention provides a probe design and two (or more) appropriate wavelengths or light emitting diodes (LED) wavelengths that will yield accurate hemoglobin concentration results. In one embodiment of the invention, an infrared LED may be used as the emitter and an identical infrared LED with an amplifier may be used as the detector or sensor. Such a system, greatly reduces the cost, reduces complexity and eliminates the need for a spectrometer, resulting in an unobtrusive piece of instrumentation that can be located in the vicinity of the operating room canister.

Referring again to FIG. 1, the spectrum analyzer 28 and pressure sensor 31, in combination with the sensor probe, determine the actual blood loss in situ during surgery. The major components of the present invention include:

It is also contemplated that two (or more) different color LED's could be used in lieu of a broad band light source, and identical LED's with electronic amplifier as detectors. For example, such a system may comprise:

1. 2 (or more) visible LEDs
2. 2 (or more) IR LEDs
3. Plastic Optical Fibers
4. Plastic Optical Fiber Beam Splitter
5. Plastic probe w/plastic fibers and a plastic pressure tube
6. Small Imbedded Computer or other digital processor The system of the present invention may also include a method for selecting optimal LED wavelengths, electrical and electronic methods for joining components and electronic circuitry coupled with a low cost digital computer (microprocessor) for providing continuous blood quantity readout. In addition, the fiber sensor could be incorporated into the manufacture of the collection container. Also, the shape and construction of the whole sensor system could be modified. Likewise, the basic concept of source, fiber configuration within the blood solution, detector and analysis can be implemented not only by variations in the analytical processing but also by use of different probe configurations.

Figure 8:
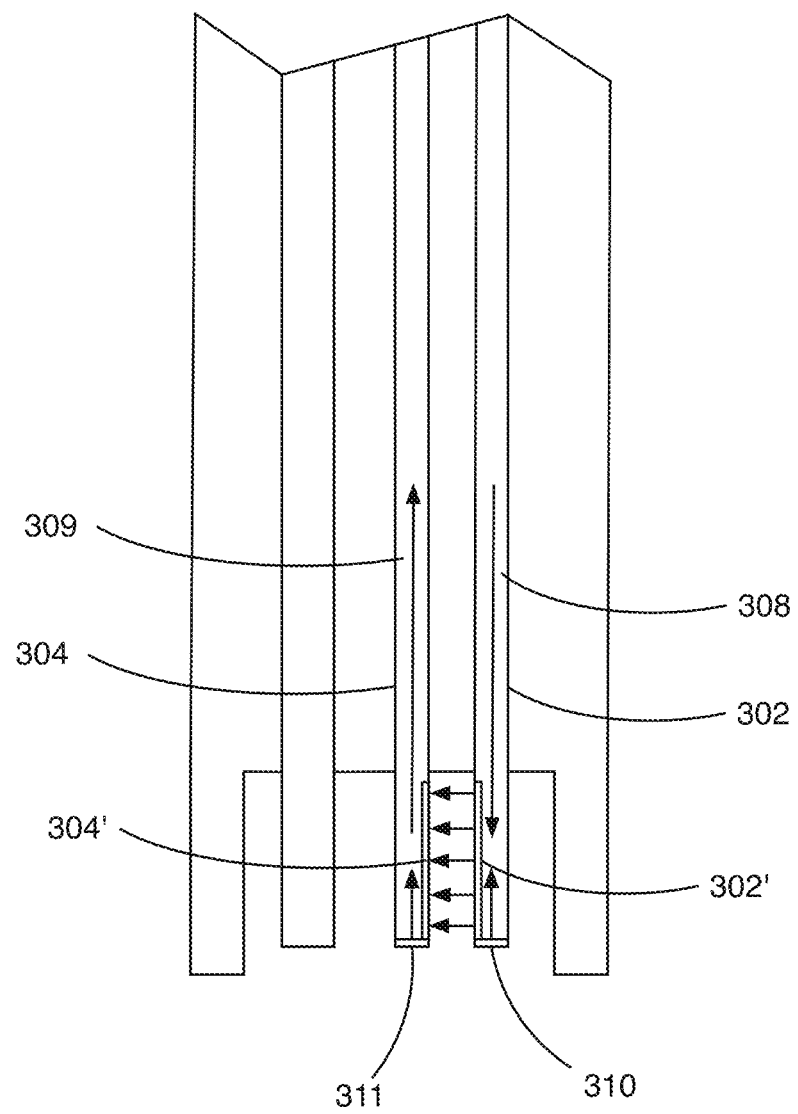
FIG. 8 is a partial front side view of another embodiment of a hemoglobin concentration and pressure sensing probe of a blood volume measuring apparatus in accordance with the principles of the present invention.

For example as shown in FIG. 8, two parallel fibers 302 and 304 with ends 302' and 304' roughened to produce scattering of light into and out of the fibers 302 and 304. These roughened sections 302' and 304' would be in the blood mixture to be measured. Light, indicated by arrows, would both pass through and be scattered from the blood volume. The parallel fibers 302 and 304, if they are optical waveguides comprised of core and cladding, could have cladding 308 and 309, respectively, removed on the facing surfaces to increase light transfer. In addition, the distal ends of the fibers 302 and 304 are provided with mirror films 310 and 311 respectively, such as an aluminum coating, to provide a reflective surface to prevent light from emanating from the distal ends of the fibers. Those roughened sections 302' and 304' can also be achieved by notches incised in the fibers which disrupt light transmission from the source and send scattered light into the fluid. Further, the physical configuration of the 302 and 304 fibers can be different, one from the other, to produce a desired wavelength transmission profile. Also, the distal end of either fiber could be polished at a selected angle and coated with highly reflective material to optimize the amount or distribution of light from the source, or similarly optimize the collection fiber.

Figure 9:
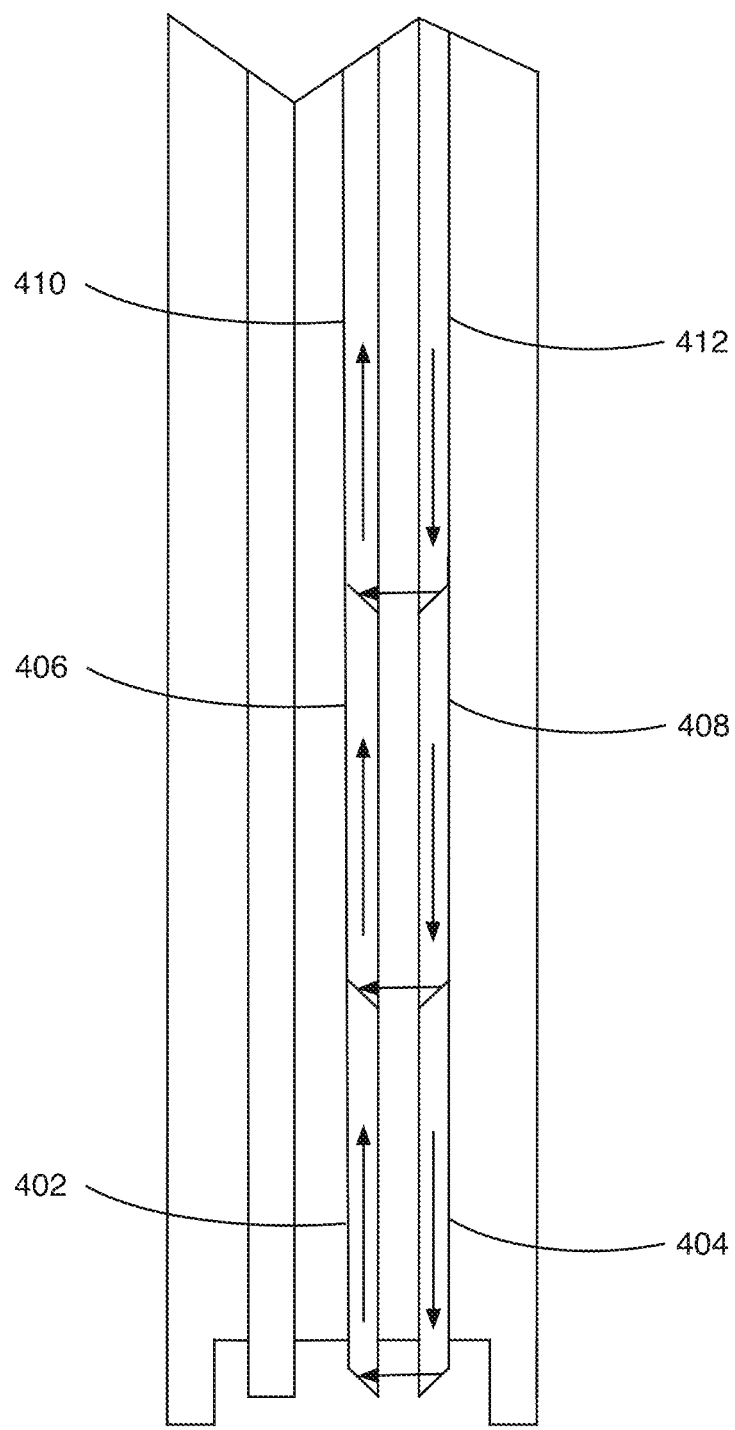
FIG. 9 is a partial front side view of yet another embodiment of a hemoglobin concentration and pressure sensing probe of a blood volume measuring apparatus in accordance with the principles of the present invention.

As shown in FIG. 9, the system may include a plurality of parallel fibers 402, 404, 406, 408, 410 and 412. Each pair of fibers has a configuration similar to the pair of fibers shown in FIG. 1. That is, each pair of fibers has angled distal ends to direct light from one fiber to the other. In addition, each pair of fibers is vertically spaced relative to each other along the probe 420. By obtaining light readings over a length of the probe 408, both a depth of the fluid in the container and average light intensity can be determined. That is, when a fiber pair is not submerged and no light absorption is detected, it can be determined that the level of fluid in the container is below that pair of fibers. In addition, for those pairs of fibers that are below the level of fluid in the container, an average or comparative hemoglobin concentration can be calculated in the event that the hemoglobin concentration of the fluid mixture is not evenly distributed within the container to obtain a more accurate reading.

A simple model illustrates the approach of using a side-emitting fiber with a parallel receiving fiber. For this it may be noted that the side-emitting fiber can be scribed, etched, cut or otherwise modified such that the intensity profile along the fiber is constant, that is, it emits a uniform distribution. The receiving fiber likewise can be modified to intercept the emitted light and transmit some fraction of that to a detector to which it is connected. A ray of light incident near the top of the receiving fiber will traverse a shorter distance within the receiving fiber than one incident near the bottom. For the limiting case where the receiving fiber conveys the received rays of light in a lossless manner, the amount of light transmitted and detected by the receiving detector will be:

$$T = \varepsilon Io(b/L)$$

where Io is the incident light emanated by the delivery fiber, $\varepsilon$ is the efficiency of capture by the receiving fiber, b is the liquid level, and L is the sensing length of the fiber sensor. This is based on the notion that light that emanates from the delivery fiber that is underneath the surface of the liquid may be mostly absorbed by the liquid. Any light rays traversing the liquid, such as a blood mixture, and which do strike the receiving fiber will not be efficiently captured and transmitted because of the approximate index of refraction matching of the blood mixture and fiber. Hence only light above the liquid level has a reasonable chance of being captured and guided inside the receiving fiber. However, the process of altering the receiving fiber to capture light that is incident from the side (whether by roughening, cuts, etc.) will also affect how it transmits light up and down its central core. There will be an effective attenuation, $\alpha$. A first order analysis assumes the common exponential dependence. Consider that for a differential length segment, dl, of the receiving fiber there will be a corresponding differential value of intensity of the form dl. The total attenuation of this differential element of light traveling through the fiber will be:

$$dI = \varepsilon \left(\frac{Io}{L}\right) \exp(-\alpha l) dl$$

The total signal that will be received by a detector from all the differential elements will be the integral from the location of the liquid surface, b, to the full length of the sensor, L.

$$T = \int_b^L dI = \frac{\varepsilon Io}{\alpha L} \int_b^L e^{-\alpha l} dl = \frac{\varepsilon Io}{\alpha L(e^{-\alpha b} - e^{-\alpha L})}$$

Figure 10:
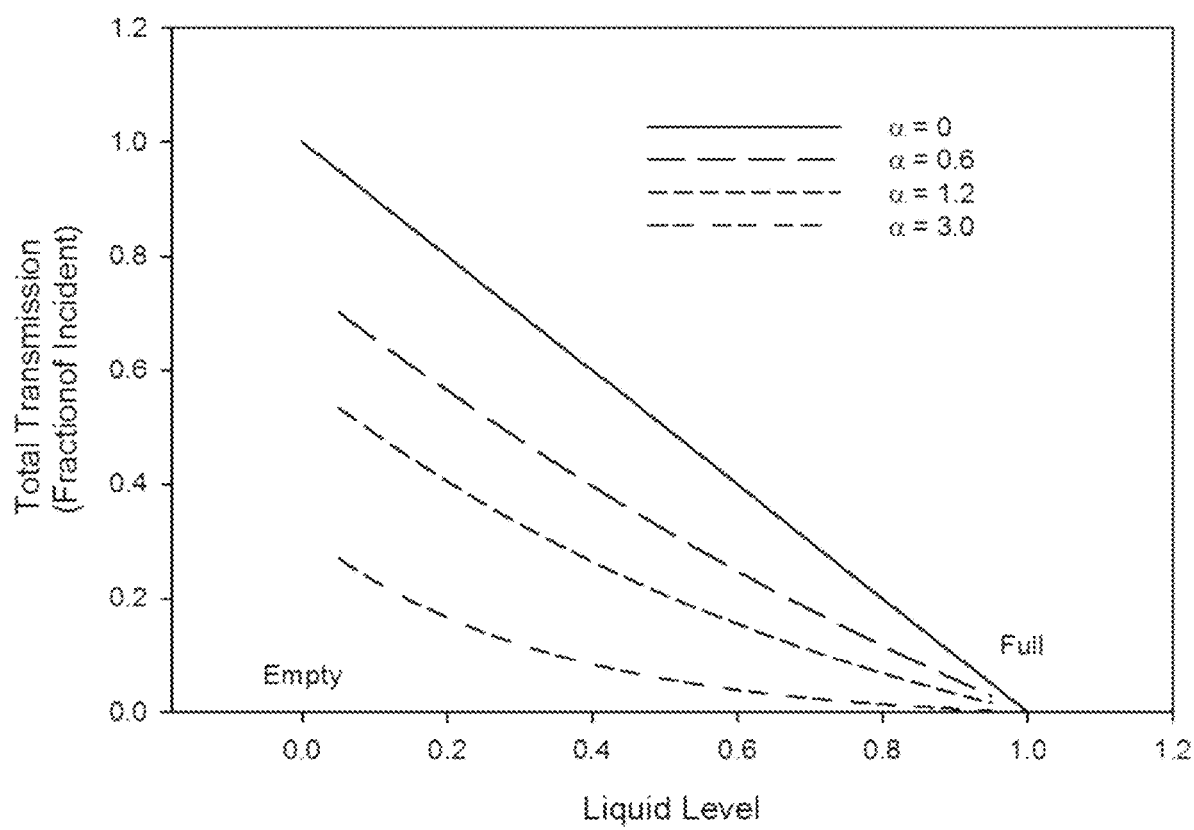
FIG. 10 is a graph showing a received signal versus a blood liquid level of a blood volume measuring apparatus in accordance with the principles of the present invention.

To illustrate this further, FIG. 10 is a graph of several hypothetical values of attenuation, $\alpha$(0, 0.6, 1.2, and 3.0) using the equation above. The equations are normalized to unit values of initial intensity and sensor length. The value of $\varepsilon$ in the equation is simply a constant scale factor in this simplified case. As shown in FIG. 10, the received signal (Total Transmission) based on the fraction of incident is a single-valued function of the liquid level. Also, as the attenuation increases, the overall range of the total transmission is reduced. For example, for an attenuation of 0, the total transmission ranges from 1.0 for an empty canister to 0.0 for a full canister. For an attenuation of 3.0, however, the total transmission ranges from about 0.3 for an empty canister to 0.0 for a full canister. This analysis applies to the design for which downward scattered light is highly attenuated and is not reflected back. It is also the case that these results can be modified and optimized by judiciously altering the side-emitting fiber's light distribution to be non-uniform in a way that is advantageous to the present invention.

It is further contemplated that two parallel fibers with polished ends pointing to a reflecting surface (such as aluminum) could be employed. The gap between fiber ends and the reflective surface would be well defined and filled with the blood mixture to be measured. In this case, both transported light (from down and back reflectance) and scattered light would be measured. It is also contemplated that a single contiguous fiber or two fibers which are bent around a tight radius of curvature in the blood mixture to be measured could be utilized in accordance with the principles of the present invention. A notch (for a contiguous fiber) or (for two fibers) a space would be provided for receiving the blood mixture in the canister. The resulting notch would be triangular in shape so that the optical paths exiting the light-source fiber would vary in length. Both the curved shape and non-uniform gap would allow a different, possibly more sensitive, combination of transport and scattering into the collection fiber.

It is further noted that any of the fiber arrangements set forth herein, coupled with the configuration used for depth, can be contained in an integrated instrumented canister. The canister would have connections at the top for both the optical and pressure measurements, in addition to the usual connections for the vacuum source, if needed, and blood entrance.

In a further exemplary aspect, the processor of the system can be configured to receive one or more user inputs, with each input corresponding to at least one of the following variables: Estimated Blood Loss (EBL) of the subject; Volume of the fluid sample; hemoglobin concentration of the blood of the subject; Estimated Blood Volume (EBV) of the subject; and volume of N fluid administered to the subject.

In a further exemplary aspect, a blood measurement system comprises the blood measurement device of any one of the previously described aspects and a suction canister, the suction canister having an outer wall having an internal surface and an external surface, the internal surface of the outer wall defining an interior space configured to receive the probe.

In another exemplary aspect, the probe is integrally formed with the suction canister.

In another exemplary aspect, the blood measurement system further comprises a drip counter configured for communication with an intravenous (N) fluid delivery element, the drip counter is configured to produce a volume signal indicative of the volume of IV fluid dispensed from the N fluid delivery element and a delivery rate signal indicative of the rate at which IV fluid is dispensed from the IV fluid delivery element, and the drip counter is positioned in operative communication with the processor such that the processor is configured to receive the volume signal and the delivery rate signal.

In another exemplary aspect, the processor is configured to receive at least one user input, and each user input is indicative of one of: a volume of one or more intravenous fluids dispensed from a fluid delivery element; and a rate at which the one or more IV fluids is dispensed from the IV fluid delivery element.

In an additional exemplary aspect, a method of measuring the amount of blood of a subject within a fluid sample comprises operatively positioning a blood measurement device of any of the preceding aspects relative to a fluid sample; and using the blood measurement device to determine the concentration of hemoglobin within the fluid sample.

In another exemplary aspect, the method further comprises administering one or more reagents to the fluid sample, wherein the one or more reagents are configured to convert hemoglobin within the fluid sample into one of methemoglobin and sulphemoglobin.

In another exemplary aspect, the method further comprises delivering an anticoagulant to the fluid sample.

In another exemplary aspect, the anti-coagulant is heparin.

Although several embodiments of the invention have been disclosed in the foregoing specification, it is understood by those skilled in the art that many modifications and other embodiments of the invention will come to mind to which the invention pertains, having the benefit of the teaching presented in the foregoing description and associated drawings. It is thus understood that the invention is not limited to the specific embodiments disclosed hereinabove, and that many modifications and other embodiments are intended to be included within the scope of the appended claims. Moreover, although specific terms are employed herein, as well as in the claims that follow, they are used only in a generic and descriptive sense, and not for the purposes of limiting the described invention, nor the claims, which follow.

In the foregoing specification, the present invention has been described with reference to specific exemplary embodiments. Various modifications and changes may be made, however, without departing from the spirit and scope of the present invention as set forth in the claims. The specification and figures are illustrative, not restrictive, and modifications are intended to be included within the scope of the present invention. Accordingly, the scope of the present invention should be determined by the claims and their legal equivalents rather than by merely the examples described.

For example, the steps recited in any method or process claims may be executed in any order and are not limited to the specific order presented in the claims. Additionally, the components and/or elements recited in any apparatus claims may be assembled or otherwise operationally configured in a variety of permutations and are accordingly not limited to the specific configuration recited in the claims.

Benefits, other advantages, and solutions to problems have been described above with regard to particular embodiments. Any benefit, advantage, solution to problem, or any element that may cause any particular benefit, advantage, or solution to occur or to become more pronounced are not to be construed as critical, required, or essential features or components of any or all the claims.

The terms "comprise", "comprises", "comprising", "having", "including", "includes" or any variations of such terms, are intended to reference a non-exclusive inclusion, such that a process, method, article, composition or apparatus that comprises a list of elements does not include only those elements recited, but may also include other elements not expressly listed or inherent to such process, method, article, composition or apparatus. Other combinations and/or modifications of the above-described structures, arrangements, applications, proportions, elements, materials, or components used in the practice of the present invention, in addition to those not specifically recited, may be varied or otherwise particularly adapted to specific environments, manufacturing specifications, design parameters, or other operating requirements without departing from the general principles of the same.

What is claimed is:

1. A blood loss measurement device for determining an amount of blood within a fluid sample from a patient, comprising:
    a container having a vertical axis, the container configured for receiving fluid containing blood from a patient during a surgical procedure;
    at least one light source in an operative position within the container configured to generate light at a plurality of wavelengths within the container;
    at least one light detector to detect at least a first portion of light from the at least one light source at the first wavelength from the plurality of wavelengths and at least a second portion at a second wavelength from the plurality of wavelengths that is different than the first wavelength, the at least one light detector producing a first signal indicative of a first absorbance of light of the fluid sample and a second signal indicative of a second absorbance of light of the fluid sample;
    a plurality of optical fibers comprising:
        a first optical fiber having a first end coupled to the light source and a second end opposite the first end held in the container proximate a bottom of the container; and
        a second optical fiber having a first end held within the container proximate a bottom of the container and positioned a distance from the second end of the first optical fiber so that light emanating from the first optical fiber is a least partially received by the second optical fiber and a second end coupled to the at least one light sensor, an amount of light received by the second optical fiber being detected by the at least one light sensor to detect the amount of light received by the second optical fiber from the first optical fiber at the first and second wavelengths; and
    a processor operatively coupled to the at least one light detector, the processor receiving the first and second signals from the at least one light detector, the at least one signal being dependent upon an amount of absorption of light by blood in the container disposed between the first optical fiber and second optical fibers, the processor repeatedly determining a concentration of hemoglobin in the container depending on the first and second signals as fluid from the patient is added to the fluid sample in the container.

2. The blood measuring device of claim 1, further comprising a volume detection device.

3. The blood measuring device of claim 2, wherein the volume detection device comprises at least one pressure sensor.

4. The blood measuring device of claim 3, where the at least one volume detection device comprises a tube having a first end positioned proximate a bottom surface of the container and a second end coupled to the pressure sensor, the pressure sensor generating a pressure signal and being operatively coupled to the processor, wherein the processor determines a volume of fluid within the container based on the pressure signal.

5. The blood measuring device of claim 2, where the volume detection device comprises a signal analysis of selected wavelength bands of light arising from the source, wherein the selected wavelength bands are affected by fluid depth so as to indicate a location of an interface of fluid and air in the container.

6. The blood measuring device of claim 1, wherein the first optical fiber transmits light from the light source over a portion of a longitudinal length of the first optical fiber facing the second optical fiber and above the second end of the first optical fiber and wherein the second optical fiber receives the light from the first optical fiber over a corresponding longitudinal length of the second optical fiber which faces the first optical fiber.

7. The blood measuring device of claim 1, wherein the plurality of optical fibers comprise a plurality of pairs of first and second optical fibers, each pair of first and second optical fibers having paired ends positioned at a different depth from other paired ends within the container to provide a plurality of signals from the at least one light sensor, each of the plurality of signals corresponding to a detected amount of absorption of light from one of the plurality of pairs of first and second optical fibers.

8. The blood measuring device of claim 1, wherein the transmitting end of the first optical fiber defines a first angled end surface of about 45 degrees and the receiving end of the second optical fiber defines a second angled end surface of about 45 degrees, wherein the first and second angled end surfaces are substantially horizontally aligned and angled from their respective distal ends away from each other so that light transmitted through the first optical fiber will reflect off of the first angled end surface and be directed toward the second angled end surface and be reflected off of the second angled end surface up through the second optical fiber.

9. The blood measuring device of claim 1, wherein a first longitudinal portion of the transmitting end of the first optical fiber faces the second optical fiber and is configured to transmit light there through toward the second optical fiber and wherein a second longitudinal portion of the second optical fiber faces the first longitudinal portion and is configured to receive the light from the first optical fiber.

10. The blood measurement device of claim 1, wherein the first wavelength ranges from about 500 nm to about 600 nm, and wherein the second wavelength ranges from about 850 nm to about 900 nm.

11. The blood loss measurement device of claim 1, wherein the first wavelength is about 525 nm, and wherein the second wavelength is about 870 nm.

12. The blood loss measuring device of claim 1, further comprising a housing defining at least one longitudinally extending channel for housing the first and second optical fibers and maintaining the proximate position of the first end of the first optical fiber relative to the second end of the first optical fiber.

13. The blood measurement device of claim 1, wherein the light source comprises a plurality of light emitting diodes (LEDs), wherein at least one LED of the plurality of LEDs is configured to emit light at the first wavelength, and wherein at least one LED of the plurality of LEDs is configured to emit light at the second wavelength.

14. The blood measurement device of claim 13, further comprising a plurality of pairs of opposed optical fibers, each pair of optical fibers comprising a first optical fiber operatively coupled to a corresponding LED of the plurality of LEDs and a second optical fiber operatively coupled to the at least one light detector, wherein the plurality of opposed pairs of optical fibers are configured for selective insertion within the fluid sample, and wherein in the operative position, the at least one light detector and the plurality of LEDs are not in fluid communication with the fluid sample.

15. The blood measurement device of claim 1, wherein a distance between the transmitting end of the first optical fiber and the receiving end of the second optical fiber ranges from about 0.05 mm to about 0.2 mm.

16. The blood measuring device of claim 1, wherein the concentration of hemoglobin and the volume in the container in the container is used to determine a resulting blood loss measurement and wherein the resulting blood loss measurement is used to monitor blood infusion during a surgical procedure where blood infusion is being deployed to limit excess or insufficient blood infusion to ameliorate a patient's condition during a procedure.

17. The blood measuring device of claim 16, wherein the resulting blood loss measurement is used to calculate infusion volumes of crystalloid or colloid solutions to replace blood loss during surgical procedures, to limit excess nor insufficient crystalloid/colloid infusions, which can be harmful to the patient.

18. A blood loss measurement device for determining an amount of blood of a patient within a fluid sample, the fluid sample having a volume, the blood measurement device comprising:
   a container configured to receive blood from a patient during a medical procedure;
   a plurality of light sources, each configured to generate light at a wavelength different from the other plurality of light sources;
   at least one light sensor configured to detect a first amount of light from the plurality of light sources and to generate a signal of the first amount of light;
   a plurality of optical fibers comprising:
      a first plurality of optical fibers each having a first end coupled to at least one of the plurality of light sources and a second end opposite the first end configured to be disposed within the container proximate a bottom of the container; and
      a second optical fiber having a first end proximate to and spaced a distance from the second end of the first optical fiber and positioned to receive light from the first optical fiber and a second end coupled to the at least one light sensor, wherein light emanating from the first optical fiber is a least partially received by the second optical fiber, the amount of light received by the second optical fiber being detected by the at least one light sensor to determine an amount of light received by the second optical fiber from the first optical fiber;
   a processor operatively coupled to the at least one light sensor, the processor configured to receive the signal from the at least one light sensor, the signal being dependent upon an amount of absorption of light by blood in the container disposed between the first optical fiber and the second optical fiber and the processor determining a concentration of blood in the container depending on the signal;
   and a volume detection device for continually detecting a volume of fluid in the container as fluid is added to the fluid sample.

19. The blood measuring device of claim 18, wherein the first optical fiber transmits light from the light source over a portion of a longitudinal length of the first optical fiber facing the second optical fiber and above the second end of the first optical fiber and wherein the second optical fiber receives the light from the first optical fiber over a corresponding longitudinal length of the second optical fiber above the first end of the second optical fiber which faces the first optical fiber.

20. The blood measuring device of claim 18, wherein the plurality of optical fibers comprise a plurality of pairs of first and second optical fibers, each pair of first and second optical fibers positioned at a different depth within the container to provide a plurality of signals from the at least one light sensor, each of the plurality of signals corresponding to a detected amount of absorption of light from one of the plurality of pairs of first and second optical fibers.

* * * * *